United States Patent
Ding et al.

(10) Patent No.: US 6,733,997 B1
(45) Date of Patent: May 11, 2004

(54) ISOLATED NUCLEIC ACIDS ENCODING A SECRETORY SIGNAL FOR EXPRESSION AND SECRETION OF HETEROLOGOUS RECOMBINANT PROTEINS

(75) Inventors: Jeak Ling Ding, Singapore (SG); Nguan Soon Tan, Singapore (SG); Bow Ho, Singapore (SG); Toong Jin Lam, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 09/426,776

(22) Filed: Oct. 26, 1999

Related U.S. Application Data

(60) Provisional application No. 60/106,426, filed on Oct. 30, 1998.

(51) Int. Cl.[7] .................. A61K 39/395; A61K 39/40; A61K 39/42; C12P 21/04; C12P 7/18
(52) U.S. Cl. .............. 435/69.8; 424/134.1; 424/145.1; 424/185.1; 424/192.1; 435/69.9; 435/70.1; 435/70.2; 435/158; 435/172; 435/173; 435/332; 436/86.89; 530/300; 536/23.1; 930/300; 930/310
(58) Field of Search .................. 485/269.8, 69.9, 485/70.1, 70.2, 158, 172, 173; 486/86.89; 530/300; 980/300, 310

(56) References Cited

U.S. PATENT DOCUMENTS 5,716,834 A  2/1998  Ding et al. ................ 435/219

OTHER PUBLICATIONS

Lim et al. Accession: AAD01615. vitellogenin [gi:4102881]. Submitted Aug. 5, 1997.*
Lim et al. 1991. Gen. and Comparative Endocrin. 82: 206–214.*
Yarranton. 1990. Current Opinion in Biotechnology. 1: 133–140.*
Ding et al. 1994. gen. and comparative Endocrin. 96: 276–287.*
LaFleur et al. Accession: U70826. Fundulus heterocl. [gi:1621358]. Submitted Sep. 15, 1996.*
Lee et al. 1994. biochem and Mol. Biol. Inter'l. 34(1): 75–83.*
Lim et al. Accession: AF017250. Oreochromis aureu . . . [gi:4102880]. Submitted Aug. 5, 1997.*
Lee et al., *Biochemistry and Molecular Biology International*, vol. 34, No. 1, pp. 75–83 (Sep. 1994).
Ding, *Biochemistry International*, vol. 20, No. 4, pp. 843–852 (1990).
Kriegler, *Methods in Enzymology*, vol. 185, No. 40, pp. 512–526 (1990).
Kaufman, *Methods in Enzymology*, vol. 185, No. 39, pp. 487–511 (1990).
Yarranton, *Current Opinion in Biotechnology*, vol. 1, pp. 133–140 (1990).

(List continued on next page.)

*Primary Examiner*—Ja-Na Hines
(74) *Attorney, Agent, or Firm*—Birch, Stewart, Kolasch & Birch, LLP.

(57) ABSTRACT

A universal secretory signal originally derived from a piscine vitellogenin (Vtg) gene is inserted into various expression vectors for driving the secretion of the recombinant protein into the culture medium. This enhances the detection, quantification and downstream scaled-up purification of a recombinant protein of interest. The secretory signal system is very versatile, being conveniently and widely applicable to an array of heterologous host cells such as bacteria, yeast, insect, piscine, and mammalian cell lines (e.g., COS, CHO, NIH/3T3). The said secretory system is also applicable as a reporter vector for secretion of reporter proteins/enzymes, thus, enabling the detection of the reporter proteins (e.g., CAT, GFP) in the culture medium.

25 Claims, 27 Drawing Sheets

OTHER PUBLICATIONS

Ding et al., *Molecular Marine Biology and Biotechnology*, vol. 4, No. 1, pp. 90–103 (1995).

Lemontt et al., *DNA*, vol. 4, No. 6, pp. 419–428 (1985).

Pui et al., *Journal of Endotoxin Research*, vol. 4, No. 6, pp. 391–400 (1997).

Martegani et al., *Appl. Microbiol. Biotechnol.*, vol. 37, pp. 604–608 (1992).

van der Straten et al., *Invertebrate Cell System Applications*, vol. 1, pp. 183–195 (1989).

Lewin B., *Genes V* (*book*), pp. 289–295 (1994).

Lewin, B., *Genes V* (*book*), pp. 298–299 (1994).

Barritt, GJ, *Communication with Animal Cells* (*Book*), pp. 42–48 (1992).

* cited by examiner

```
5'
GTG GAA TTC TGC AGA TGC TAC CGG ACT CAG ATC AAT TCA CAT CCA CCA GCC
ATG AGG GTG CTT GTA CTA GCT CTT GCT GTG GCT CTC GCA GTG GGG GAC CAG
 M   R   V   L   V   L   A   L   A   V   A   L   A   V   G   D   Q
 ──OaVtgss──▶                                              ▲
                                                      Cleavage site TCC AAC TTG GGG GAT CTA GGC TTG TGT GAT GAA ACG AGG TTC GAG TGT AAG
 S   N   L   G   D   L   G   L   C   D   E   T   R   F   E   C   K
                     ──Factor C──▶

TGT GGC GAT CCA GGC TAT GTG TTC AAC ATT CCA GTG AAA CAA TGT ACA TAC 3'
 C   G   D   P   G   Y   V   F   N   I   P   V   K   Q   C   T   Y
``` pAc5/VtgCrFCES-V5-His

FIG.2A

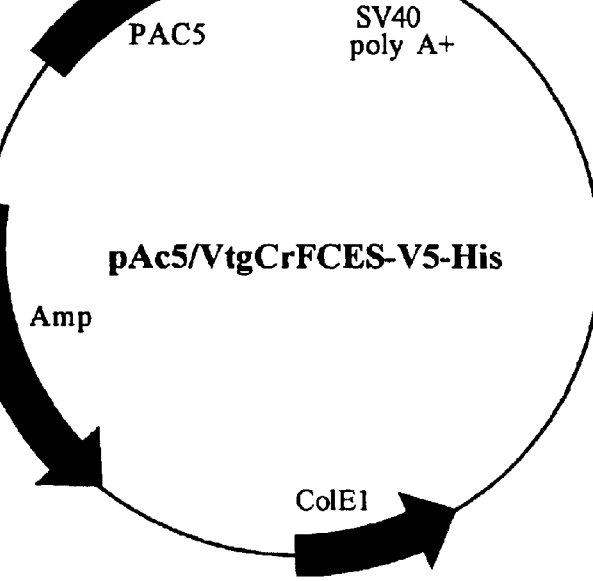

FIG.2B

```
5'
        Hind III  Eco RV/Eco 47III
ATC GAT AAG CTT GAT GCT ACC GGA CTC AGA TCA ATT CAC ATC CAC CAG CC ATG AGG GTG CTT GTA CTA GCT CTT GCT GTG GCT CTC GCA GTG GGG GAC CAG
 M   R   V   L   V   L   A   L   A   V   A   L   A   V   G   D   Q
─OaVtgss──▷                                                  ⋀
                                                          Cleavage site Bgl II/Bam HI
TCC AAC TTG GGG GAT CTG CTG GAG AAA AAA ATC ACT GGA TAT ACC ACC GTT
 S   N   L   G   D   L   L   Q   K   K   V   T   G   W   T   T   V
                         ─CAT──▷
                                                      Eag I
ooo ooo ooo GGC GGG GCG TAA TTT TTT TAA GGC ACG GCC GAT GCG ACG
             G   G   A  ***
  Cla I
GTA TCG ATA ACT TGA TAT CG 3'
        Hind III
                                                          pBSVtgCAT
```

FIG.5B

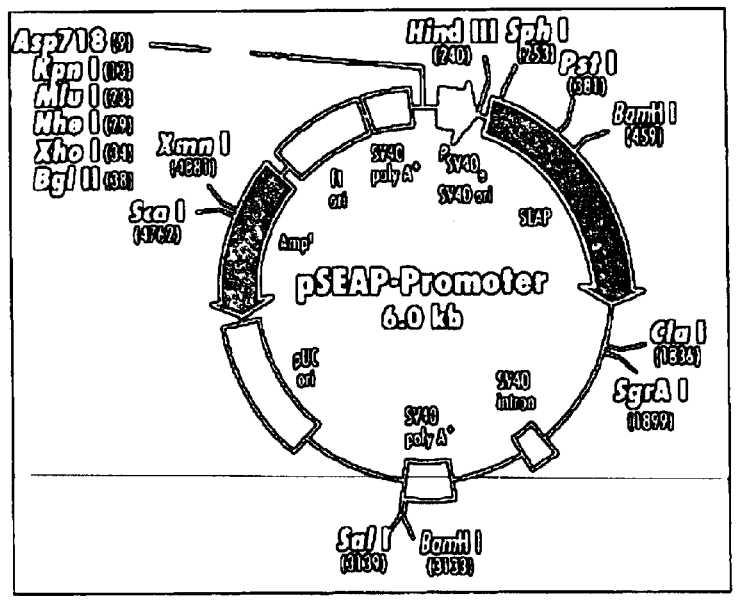

FIG.5C

```
5'
         Hind III   Eco RV/Eco 47III
TGC AAA AAG CTT GAT GCT ACC GGA CTC AGA TCA ATT CAC ATC CAC CAG CC ATG AGG GTG CTT GTA CTA GCT CTT GCT GTG GCT CTC GCA GTG GGG GAC CAG
 M   R   V   L   V   L   A   L   A   V   A   L   A   V   G   D   Q
─OaVtgss──▶                                                ▲
                                                      Cleavage site Bgl II/Bam HI
TCC AAC TTG GGG GAT CTG CTG GAG AAA AAA ATC ACT GGA TAT ACC ACC GTT
 S   N   L   G   D   L   L   Q   K   K   V   T   G   W   T   T   V
                      ──CAT──▶
                                                    Eag I
··· ··· ··· GGC GGG GCG TAA TTT TTT TAA GGC ACG GCC GAT GCG ACG
             G   G   A  ***
   Cla I
GTA TCG ATA TTG TTA CAA CAC CCC AAC 3'
``` psp-VtgCAT

FIG.5D

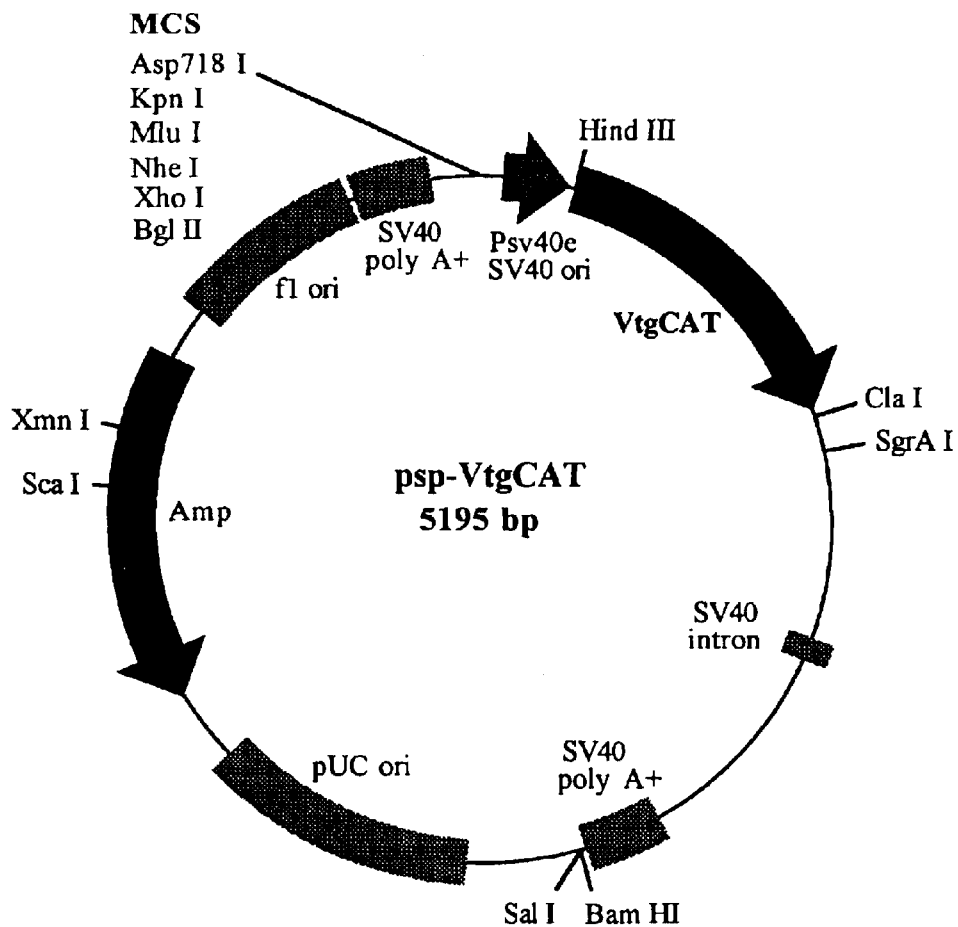

FIG.5E

```
5'
Nhe I                                          +1
GCT AGC GCT ACC GGA CTC AGA TCA ATT CAC ATC CAC CAG CC
    Eco 47 III

ATG AGG GTG CTT GTA CTA GCT CTT GCT GTG GCT CTC GCA GTG GGG GAC CAG
 M   R   V   L   V   L   A   L   A   V   A   L   A   V   G   D   Q
OaVtgss ──▶

Bam HI   Age I
TCC AAC TTG GGG GAT CCA CCG GTC GCC ACC ATG GTG AGC AAG GGC GTG GTG
 S   N   L   G   D   P   P   V   A   T   M   V   S   K   G   V   V
                                         EGFP ──▶

CAG AAC TCC GGG 3'
 Q   N   S   G
                                                        pVtgEGFP
```

```
5'                                                          BspHI/NcoI
CTC TAC TGT TTC TCC ATA CCC GTT TTT TTG GGC TAA CAG GAG GAA TTA ACC

ATG AGG GTG CTT GTA CTA GCT CTT GCT GTG GCT CTC GCA GTG GGG GAC CAG
 M   R   V   L   V   L   A   L   A   V   A   L   A   V   G   D   Q
   OaVtgss →                                              Cleavage site
              Bam HI
TCC AAC TTG GGG GAT CCA GAA ACG CTG GTG AAA GTA AAA GAT GCT GAA GAT
 S   N   L   G   D   P   E   T   L   V   K   V   K   D   A   E   D
                    β-lactamase →

CAG TTG GGT GCA CGA GTG GGT TAC ATC GAA CTG GAT CTC AAC AGC GGT AAG 3'
 Q   L   G   A   R   V   G   Y   I   E   L   D   L   N   S   G   K pBADVtgblactKana
```

FIG. 14A

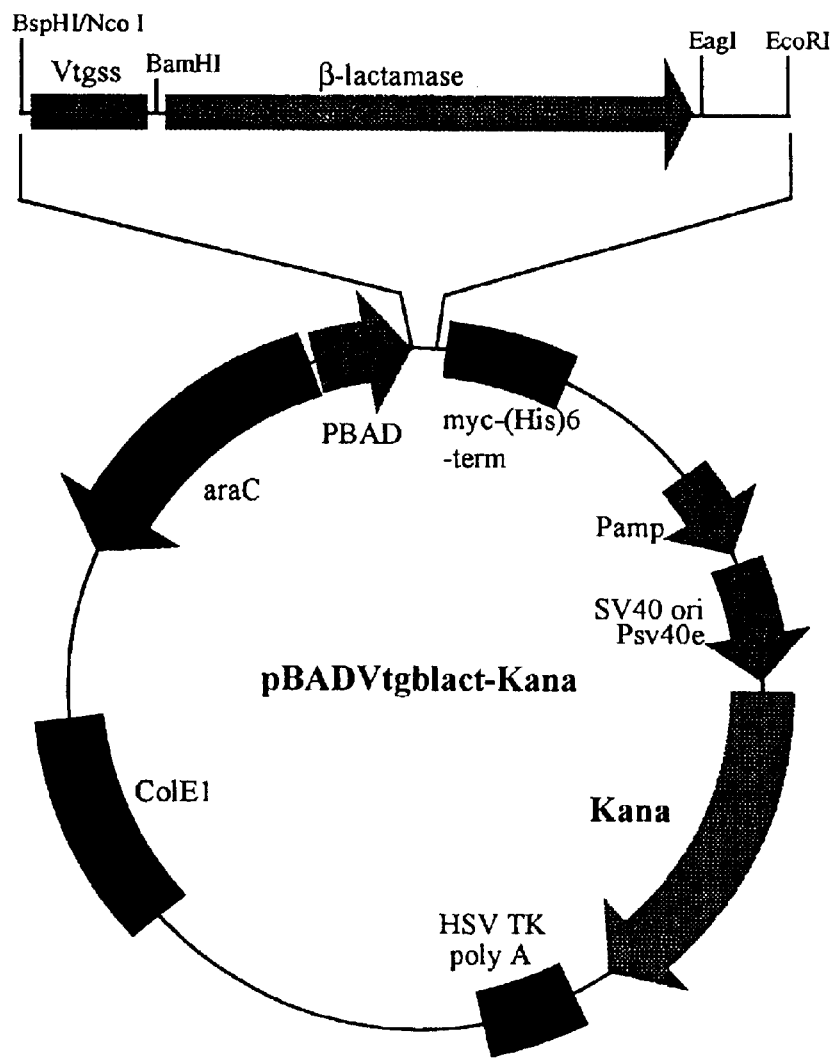

FIG. 14B

SEQUENCE LISTING

<160> NUMBER OF SEQ ID NOS: 22

<210> SEQ ID NO 1
<211> LENGTH: 29
<212> TYPE: DNA
<213> ORGANISM: Artificial Sequence
<220> FEATURE:
<223> OTHER INFORMATION: Chloramphenicol acetyltransferase (CAT) gene
      forward primer derived from bacteria

<400> SEQUENCE: 1
gaagatctgc tggagaaaaa aatcactgg                               29

<210> SEQ ID NO 2
<211> LENGTH: 29
<212> TYPE: DNA
<213> ORGANISM: Artificial Sequence
<220> FEATURE:
<223> OTHER INFORMATION: Chloramphenicol acetyltransferase (CAT) gene
      forward primer derived from bacteria

<400> SEQUENCE: 2
gcatcggccg tgccttaaaa aaattacgc                               29

<210> SEQ ID NO 3
<211> LENGTH: 21
<212> TYPE: DNA
<213> ORGANISM: Artificial Sequence
<220> FEATURE:
<223> OTHER INFORMATION: OaVtgExon2 reverse primer derived from
      Oreochromis aureus vitellogenin gene exon 2

<400> SEQUENCE: 3
ccaagttgga ctggtccccc a                                       21

<210> SEQ ID NO 4
<211> LENGTH: 19
<212> TYPE: DNA
<213> ORGANISM: Artificial Sequence
<220> FEATURE:
<223> OTHER INFORMATION: EGFP reverse primer derived from Aequoria
      victoria green fluorescent protein

<400> SEQUENCE: 4
ccctcgccgg acacgctga                                          19

<210> SEQ ID NO 5
<211> LENGTH: 29
<212> TYPE: DNA
<213> ORGANISM: Artificial Sequence
<220> FEATURE:
<223> OTHER INFORMATION: B-lactamase forward primer derived from
      bacteria

<400> SEQUENCE: 5
ccgggatcca gaaacgctgg tgaaagtaa                               29

<210> SEQ ID NO 6
<211> LENGTH: 29
<212> TYPE: DNA
<213> ORGANISM: Artificial Sequence
<220> FEATURE:
<223> OTHER INFORMATION: B-lactamase reverse primer derived from
      bacteria

<400> SEQUENCE: 6
gcggccgtta ccaatgctta atcagtgag                                    29

<210> SEQ ID NO 7
<211> LENGTH: 29
<212> TYPE: DNA
<213> ORGANISM: Artificial Sequence
<220> FEATURE:
<223> OTHER INFORMATION: Forward primer from BspSS

<400> SEQUENCE: 7
gggtcatgag ggtgcttgta ctagctctt                                    29

<210> SEQ ID NO 8
<211> LENGTH: 30
<212> TYPE: DNA
<213> ORGANISM: Artificial Sequence
<220> FEATURE:
<223> OTHER INFORMATION: BamGal forward primer with BamHI restriction
      site and some beta-galactosidase sequence derived from bacteria

<400> SEQUENCE: 8
ccatggatcc cgtgatttcg ttgccggtct                                   30

<210> SEQ ID NO 9
<211> LENGTH: 26
<212> TYPE: DNA
<213> ORGANISM: Artificial Sequence
<220> FEATURE:
<223> OTHER INFORMATION: EagGal reverse primer with EagI restriction
      site

<400> SEQUENCE: 9
gcgacggccg ggcagacatg gcctgc                                       26

<210> SEQ ID NO 10
<211> LENGTH: 21
<212> TYPE: PRT
<213> ORGANISM: Oreochromis aureus

<400> SEQUENCE: 10

Met Arg Val Leu Val Leu Ala Leu Ala Val Ala Leu Ala Val Gly Asp
1               5                   10                  15

Gln Ser Asn Leu Gly
            20

<210> SEQ ID NO 11
<211> LENGTH: 80
<212> TYPE: DNA
<213> ORGANISM: Oreochromis aureus
<220> FEATURE:
<221> NAME/KEY: CDS
<222> LOCATION: (18)..(80)
<223> OTHER INFORMATION: Nucleotides 18-80 encode for SEQ ID NO: 10

<400> SEQUENCE: 11
attcacatcc accagcc atg agg gtg ctt gta cta gct ctt gct gtg gct    50
                   Met Arg Val Leu Val Leu Ala Leu Ala Val Ala
                   1               5                   10 ctc gca gtg ggg gac cag tcc aac ttg ggg                           80
Leu Ala Val Gly Asp Gln Ser Asn Leu Gly
            15                  20

<210> SEQ ID NO 12
<211> LENGTH: 204
<212> TYPE: DNA

<213> ORGANISM: Artificial Sequence
<220> FEATURE:
<223> OTHER INFORMATION: Junction of Vtgss (derived from Oreochromis
aureus) and CrFCES (Carcinoscorpius rotundicauda ES -
EcoRI-SalI flanking fragment of Factor C) determined by sequencing
using the Ac5 forward primer and pcDNA3.1/BGH reverse primer

<400> SEQUENCE: 12
gtggaattct gcagatgcta ccggactcag atcaattcac atccaccagc catgagggtg      60
cttgtactag ctcttgctgt ggctctcgca gtgggggacc agtccaactt ggggatcta       120 ggcttgtgtg atgaaacgag gttcgagtgt aagtgtggcg atccaggcta tgtgttcaac     180
attccagtga acaatgtac atac                                              204

<210> SEQ ID NO 13
<211> LENGTH: 51
<212> TYPE: PRT
<213> ORGANISM: Artificial Sequence
<220> FEATURE:
<223> OTHER INFORMATION: VtgCrFCES protein - Vtg derived from
Oreochromis aureus and CrFCES derived from Carcinoscorpius
rotundicauda ES - EcoRI-SalI flanking fragment of Factor C

<400> SEQUENCE: 13

Met Arg Val Leu Val Leu Ala Leu Ala Val Ala Leu Ala Val Gly Asp
1               5                   10                  15

Gln Ser Asn Leu Gly Asp Leu Gly Leu Cys Asp Glu Thr Arg Phe Glu
            20                  25                  30

Cys Lys Cys Gly Asp Pro Gly Tyr Val Phe Asn Ile Pro Val Lys Gln
        35                  40                  45

Cys Tyr Phe
    50

<210> SEQ ID NO 14
<211> LENGTH: 152
<212> TYPE: DNA
<213> ORGANISM: Artificial Sequence
<220> FEATURE:
<223> OTHER INFORMATION: Part of the Vtgss-CAT (Vtgss from Oreochromis
aureus - CAT of bacterial origin) fusion in the pBSVtgCAT vector

<400> SEQUENCE: 14
atcgataagc ttgatgctac cggactcaga tcaattcaca tccaccagcc atgagggtgc      60
ttgtactagc tcttgctgtg gctctcgcag tggggggacca gtccaacttg gggatctgc      120 tggagaaaaa aatcactgga tataccaccg tt                                    152

<210> SEQ ID NO 15
<211> LENGTH: 59
<212> TYPE: DNA
<213> ORGANISM: Artificial Sequence
<220> FEATURE:
<223> OTHER INFORMATION: Part of the Vtgss-CAT (Vtgss from Oreochromis
aureus - CAT of bacterial origin) fusion in the pBSVtgCAT vector

<400> SEQUENCE: 15 ggcgggcgt aatttttta aggcacggcc gatgcgacgg tatcgataac ttgatatcg        59

<210> SEQ ID NO 16
<211> LENGTH: 34
<212> TYPE: PRT
<213> ORGANISM: Artificial Sequence
<220> FEATURE:
<223> OTHER INFORMATION: Part of the Vtgss-CAT (Vtgss from Oreochromis
aureus - CAT of bacterial origin) fusion in the pBSVtgCAT vector

```
<400> SEQUENCE: 16

Met Arg Val Leu Val Leu Ala Leu Ala Val Ala Leu Ala Val Gly Asp
1               5                   10                  15

Gln Ser Asn Leu Gly Asp Leu Leu Gln Lys Lys Val Thr Gly Trp Thr
            20                  25                  30

Thr Val

<210> SEQ ID NO 17
<211> LENGTH: 3
<212> TYPE: PRT
<213> ORGANISM: Artificial Sequence
<220> FEATURE:
<223> OTHER INFORMATION: Part of the Vtgss-CAT (Vtgss from Oreochromis
      aureus - CAT of bacterial origin) fusion in the pBSVtgCAT vector

<400> SEQUENCE: 17

Gly Gly Ala
1

<210> SEQ ID NO 18
<211> LENGTH: 66
<212> TYPE: DNA
<213> ORGANISM: Artificial Sequence
<220> FEATURE:
<223> OTHER INFORMATION: Part of the nucleotide sequence adjoining
      Vtgss (derived from Oreochromis aureus) and CAT (derived from
      bacteria) in the vector psp-VtgCAT

<400> SEQUENCE: 18
ggcggggcgt aattttttta aggcacggcc gatgcgacgg tatcgatatt gttacaacac      60
cccaac                                                                66

<210> SEQ ID NO 19
<211> LENGTH: 155
<212> TYPE: DNA
<213> ORGANISM: Artificial Sequence
<220> FEATURE:
<223> OTHER INFORMATION: Nucleotide sequence of the Vtg-EGFP (Vtg
      derived from Oreochromis aureus - EGFP derived from Aequoria
      victoria) fusion in the vector pVtgEGFP

<400> SEQUENCE: 19
gctagcgcta ccggactcag atcaattcac atccaccagc catgagggtg cttgtactag      60
ctcttgctgt ggctctcgca gtggggggacc agtccaactt ggggggatcca ccggtcgcca    120 ccatggtgag caagggcgtg gtgcagaact ccggg                                155

<210> SEQ ID NO 20
<211> LENGTH: 38
<212> TYPE: PRT
<213> ORGANISM: Artificial Sequence
<220> FEATURE:
<223> OTHER INFORMATION: Amino acid sequence of the Vtg-EGFP (Vtg
      derived from Oreochromis aureus - EGFP derived from Aequoria
      victoria) fusion in the vector pVtgEGFP

<400> SEQUENCE: 20

Met Arg Val Leu Val Leu Ala Leu Ala Val Ala Leu Ala Val Gly Asp
1               5                   10                  15

Gln Ser Asn Leu Gly Asp Pro Pro Val Ala Thr Met Val Ser Lys Gly
            20                  25                  30

Val Val Gln Asn Ser Gly
        35
```

```
<210> SEQ ID NO 21
<211> LENGTH: 204
<212> TYPE: DNA
<213> ORGANISM: Artificial Sequence
<220> FEATURE:
<223> OTHER INFORMATION: Nucleotide sequence at the junction of Vtgss
      (derived from Oreochromis aureus) and B-lactamase (derived
      from bacteria) in pBADVtgblactKana

<400> SEQUENCE: 21
ctctactgtt tctccatacc cgtttttttg ggctaacagg aggaattaac catgagggtg      60
cttgtactag ctcttgctgt ggctctcgca gtgggggacc agtccaactt gggggatcca     120
gaaacgctgg tgaaagtaaa agatgctgaa gatcagttgg gtgcacgagt gggttacatc     180
gaactggatc tcaacagcgg taag                                            204

<210> SEQ ID NO 22
<211> LENGTH: 51
<212> TYPE: PRT
<213> ORGANISM: Artificial Sequence
<220> FEATURE:
<223> OTHER INFORMATION: Amino acid sequence at the junction of Vtgss
      (derived from Oreochromis aureus) and B-lactamase (derived from
      bacteria) in pBADVtgblactKana

<400> SEQUENCE: 22

Met Arg Val Leu Val Leu Ala Leu Ala Val Ala Leu Ala Val Gly Asp
1               5                   10                  15

Gln Ser Asn Leu Gly Asp Pro Glu Thr Leu Val Lys Val Lys Asp Ala
            20                  25                  30

Glu Asp Gln Leu Gly Ala Arg Val Gly Tyr Ile Glu Leu Asp Leu Asn
        35                  40                  45

Ser Gly Lys
    50
```

ISOLATED NUCLEIC ACIDS ENCODING A SECRETORY SIGNAL FOR EXPRESSION AND SECRETION OF HETEROLOGOUS RECOMBINANT PROTEINS

This application claims the benefit of 60/106,426, filed Aug. 30, 1998.

FIELD OF THE INVENTION

The present invention relates to the use of nucleic acids (termed "SS" for "secretory signal" or "Vtgss" for "vitellogenin secretory signal") that function as universal secretory signals for rapidly directing recombinant proteins out of a heterologous host cell. The invention is also applicable to improved and more convenient means of detecting reporter proteins by simply sampling culture medium in which cells harboring constructs of the invention are maintained. The invention is also applicable to biosensor technology, to for screening of genetically-engineered clones harboring selectable marker(s) to be expressed as an indicator, and to achieving systemic circulation/distribution of recombinant proteins in a transgenic or chimeric host organism.

DESCRIPTION OF THE RELATED ART

Although protein expression in bacteria is commonly used to obtain recombinant proteins, bacterial hosts present several drawbacks to expression of recombinant proteins. First, eukaryotic proteins expressed in *E. coli* are often not properly folded and thus non-functional (Cleland, J. L. 1993, In Protein Folding In Vivo and In Vitro: pp. 1–21). This is a large problem, since most proteins used for pharmaceutical/diagnostic purposes are eukaryotic in nature. Second, proteins expressed in large amounts in *E. coli* often precipitate into insoluble aggregates called "inclusion bodies", from which they can only be recovered in an active form by solubilization in denaturing agents followed by careful renaturation (Chang and Swartz, 1993, in "Protein Folding In Vivo and In Vitro", Cleland, J. L. ed., pp. 178–188). Third, it is difficult to engineer the secretion of large amounts of expressed protein in *E. coli*, although it has often been possible to secrete small amounts into the periplasmic space and to recover them by osmotic shock. Finally, the recovered recombinant protein is usually contaminated with an unacceptable level of endotoxin/pyrogen that makes proteins for pharmaceutical/diagnostic use extremely difficult to validate (Walsh and Headon, 1994, in "Protein Biotechnology", pp. 118–162).

Although, protein expression in yeast (*Saccharomyces cerevisiae*) can solve some of the problems associated with bacterial expression, the harsh conditions necessary to lyse the yeast often result in poor yield and denaturation of the recombinant proteins. Secretion of recombinant proteins from yeast has largely been a trial and error effort. Furthermore, most secreted proteins are trapped in the yeast periplasmic space and thus, difficult to retrieve (Lemontt et al., DNA 4:419–428 (1985); Martegani et al., *Appl. Microbiol. Biotechnol.* 37:604–608 (1992)).

The mammalian and insect expression systems have a number of advantages that have contributed to the recent popularity (Straten et al., 1989, in "Invertebrate Cell Systems Applications", pp. 183–193; Yarranton, G. T., *Curr. Opinion Biotech.* 1:133–140 (1990)). Recombinant proteins are almost always expressed at high levels and the expressed proteins are usually properly modified and accumulated in the proper cellular compartment. However, there have been occasions where the use of the homologous secretory signal of the gene insert resulted in mistargetting of the expressed proteins, which consequently remained within the yeast. Generally, protein expression in higher eukaryotes such as insect cells and mammalian cells is challenging, time-consuming and expensive although they are suitable hosts for small- and medium-scale work.

An example of a Drosophila expression system utilizes a cell line derived from *Drosophila melanogaster*, Schneider 2 (S2) cells, and a simple plasmid vector for the expression of heterologous proteins (Ivey-Hoyle, M., *Curr. Biol.* 2:704–707 (1991)). S2 cells and mammalian cells such as CHO cells have been used to express proteins for both biochemical assays and therapeutics. In both the insect and mammalian cell systems, there is a therefore a need to employ powerful secretory signals to drive the secretion of the expressed recombinant proteins out of the heterologous host cells for easy detection, quantification and large-scale purification.

For an efficient expression system, several criteria need to be satisfied. First, the recombinant protein synthesis must be functional. Second, a reasonable yield of the protein is required to justify its usage. Third, the system must enable homogenous synthesis of the recombinant protein. Last, the system should allow easy scaling-up and subsequent downstream processing, for example, purification. Consequently, we have constructed recombinant fusion vectors that direct the secretion of heterologous proteins into the medium used to culture various host cells.

An important aspect of the study of gene regulation is assay of transcription levels observed from wild-type and mutant versions of putative cis-acting control elements in transfected mammalian cells. In most cases, the ability of the cis-acting elements to modulate transcription is not assayed directly. Instead, the cis-acting elements are joined to a reporter gene that codes for a measurable enzyme activity. The level of the enzymatic activity that accumulates during the course of an experiment is taken as a measure of the ability of the cis-acting element to regulate transcription. Although this is an indirect assay of the activity of the cis-acting elements that control transcription, it is often the only one that is practicable. A number of different genes have been used as reporters of the transcriptional activity of eukaryotic promoters. These include chloramphenicol acetyltransferase (CAT), β-galactosidase and luciferase. However, all these require lysis of the transfected cells and thus are subject to the problems associated with set-up and variability of multiple cultures.

To date, the Great EscAPE SEAP Genetic Reporter System™ (Clontech) is one available system that utilizes a secreted form of an enzyme, human placental alkaline phosphatase, as a reporter for the analysis of cis-acting DNA sequences and trans-acting factors. However, a drawback of the SEAP assay is that it has to be measured using either a fluorescent or chemiluminescent assay, requiring a fluorimeter or a luminometer. Furthermore, it requires the investigator to switch from their established protocols for CAT, β-galactosidase or luciferase.

SUMMARY OF THE INVENTION

The present invention stems from the finding that the secretory signal sequence (SS or Vtgss) of the vitellogenin gene, especially the vitellogenin gene from *Oreochromis aureus*, can be used to direct the secretion of recombinant proteins out of cells. The cells that are able to utilize the *O. aureus* SS are not particularly limited; the present inventors have found that cells of many kinds, especially eukaryotic cells, will efficiently process exogenous fusion proteins comprising the SS of the invention and secrete them from the cell.

Thus, one aspect of the present invention is isolated nucleic acids that encode a SS that provides the biological activities of directing secretion of a protein linked to the SS from a host cell and cleavage of the SS from the fusion protein at a particular point in the SS sequence. The isolated nucleic acids of the invention are easily incorporated into vectors for expression of recombinant proteins and subsequent secretion of the fusion protein, processed by appropriate cleavage of the SS portion, into the medium used to culture the host cells. An advantage of the present invention is that the secretion is very efficient regardless of the particular protein secreted or the host cell used to express the recombinant protein.

Thus, the present invention resides in part in the development of an efficient and versatile vector for high level expression and immediate secretion of recombinant proteins into serum-free medium used to culture the host cells. The host cells can be immobilized, or else easily removed from the culture, thus providing easy purification of the recombinant proteins. Also, vectors comprising the SS of the invention and a reporter gene will express and efficiently secrete the reporter proteins, thus enabling easy detection of the reporter protein, for example by sampling of the culture medium, or of an extracellular fluid in the instance of an in vivo assay.

As a result of the efficient processing conferred by SS of the present invention, the invention provides assays of gene expression levels by measuring the amount of a reporter gene that is secreted into medium used to culture cells harboring vectors of the invention. An advantage of such an assay is that cells expressing the reporter gene need not be lysed to perform the assay, allowing the assay to be used for screening of clones for expression of recombinant constructs or that are co-transformed with additional vectors.

The invention also encompasses biosensors comprising cells that are transformed with vectors according to the present invention. Such biosensors can be applied to detection of compounds present in samples by addition of the samples to media used to culture cells of the invention, followed by measurement of the activity of reporter proteins in the culture media whose expression is induced or repressed by the introduction of the compound into the medium.

The present invention can also be applied to the expression of desired proteins in transgenic or chimeric organisms in vivo. In some instances, it is desirable to obtain secretion of a protein into the extracellular spaces in an organism, including extracellular matrix, various secretory ducts, peritoneal fluid, ventricular fluid, the bloodstream or the lymphatic system. The present invention can be applied to directing secretion of a desired protein into any of these extracellular spaces.

Control of expression of a desired gene, followed by secretion of the gene product from the cell, for example in a tissue-specific manner, or in a manner inducible by treatment with a particular chemical compound, can be achieved by linkage of an appropriate promoter to a structural gene comprising nucleotides encoding the SS of the invention linked to a nucleotide sequence encoding the desired gene product.

BRIEF DESCRIPTION OF THE DRAWINGS

FIG. 2A shows the amino acid (SEQ ID NO:13) and nucleotide sequences (SEQ ID NO:12) at the junction of Vtgss and CrFCES. The nucleotide junctions were determined by sequencing using the Ac5 forward primer and pcDNA3.1/BGH reverse primer. The CrFCES is cloned in-frame with respect to Vtgss (at the 5' end) and V5-His (at the 3' end). The secreted VtgCrFCES protein was purified by affinity chromatography (TALON™, Clontech) under denaturing conditions (6M urea, 250 mM NaCl and 20 mM sodium phosphate buffer, pH7.0). The protein was transferred to a PVDF membrane in transfer buffer (10% methanol, 10 mM CAPS, pH 11.0) and its N-terminal amino acid sequence determined. Using the novel Vtgss as secretory signal, only a single cleavage point was identified (indicated by the arrow). Thus, Vtgss allows the homogenous production of secreted heterologous recombinant protein.

FIG. 2B shows a map of the plasmid pAc5/VtgCrFCES-V5-His.

FIG. 3A—culture medium

Lane M: Benchmark™ prestained marker

Lane 1: control medium (30 µg)

Lane 2: VtgCrFCES medium (not purified 30 µg)

Lane 3: VtgCrFCES (affinity purified; 1 µg)

Lane 4: VtgCrFCES (ISOprime™ purified; 1 µg)

Figure 3A:
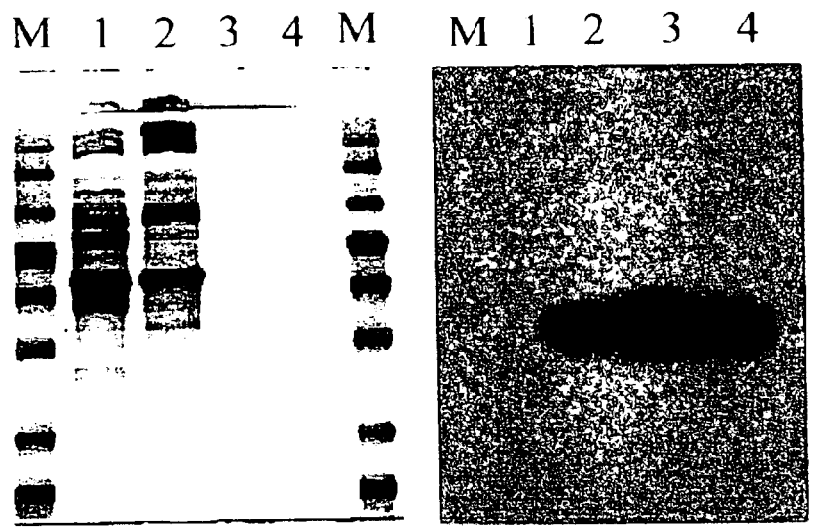
FIGS. 3A and 3B show the distribution of secreted VtgCrFCES protein.
Figure 3B:
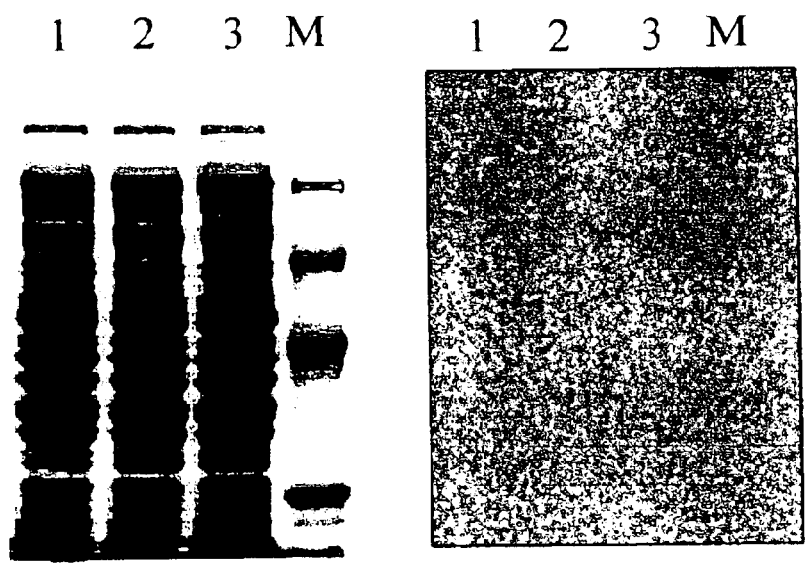

FIG. 3B—cell lysate;

Lane M: Bio-Rad prestained marker

Lane 1: control cell lysate (30 µg)

Lane 2: VtgCrFCES cell lysate (transient; 30 µg)

Lane 3: VtgCrFCES cell lysate (stable; 30 µg)

The VtgCrFCES (hereinafter "VtgCrFCES") protein was effectively secreted into the culture medium, as verified by SuperSignal HisProbe™ Western Blotting Kit (Pierce). The secreted VtgCrFCES was purified to homogeneity by isoelectric focusing (ISOprime™, Hoefer) resulting in a single protein band having a molecular weight identical to that of the protein isolated by affinity column chromatography. The ISOprime™-purified protein was not denatured even when purified in pyrogen-free water. No VtgCrFCES was detected in the cell lysate. The purification process was made easy and more effective by the presence of VtgCrFCES in the culture medium.

Figure 4:
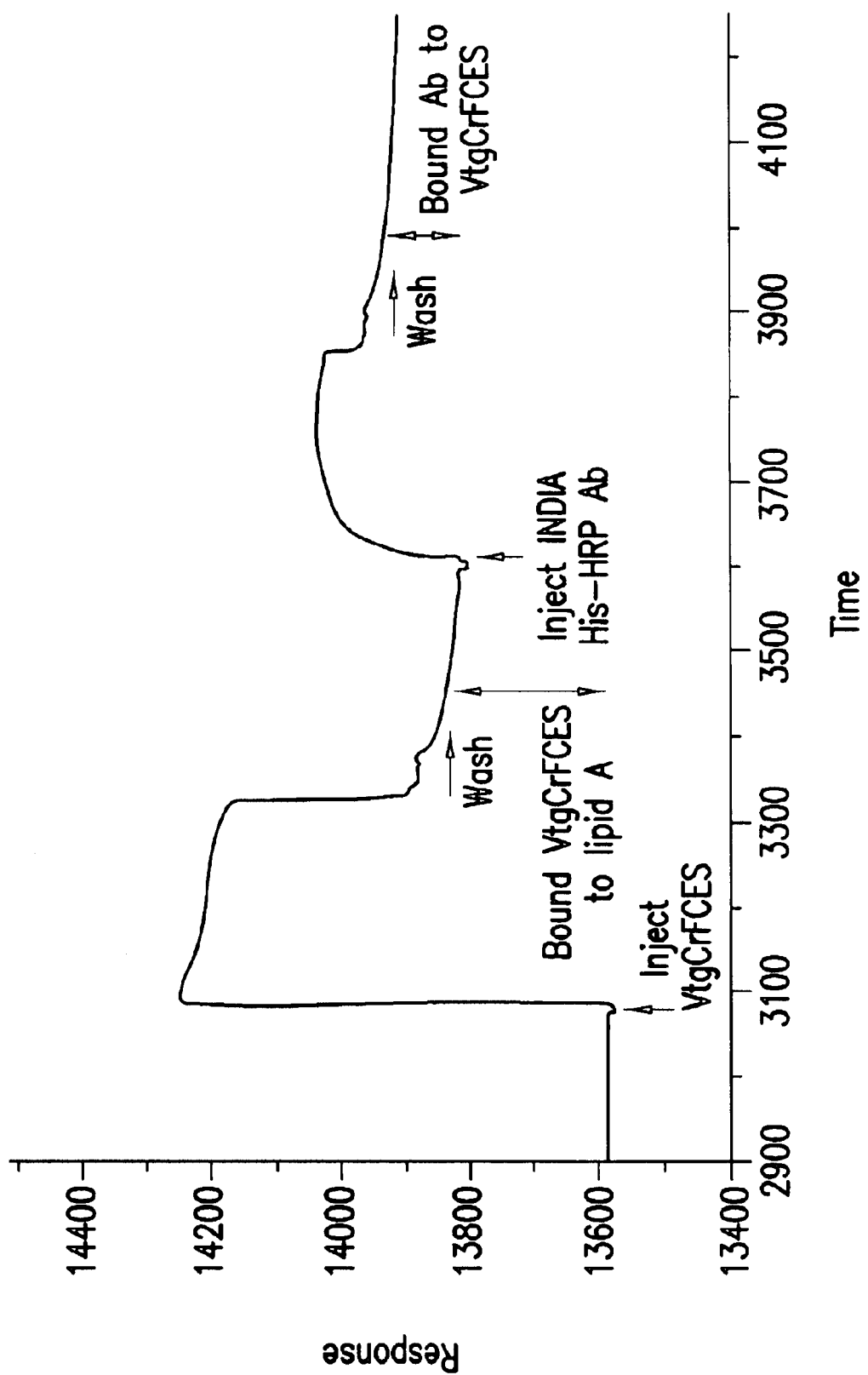

FIG. 4 shows the lipid A binding properties of ISOprime™-purified VtgCrFCES. Immobilization of lipid A to the HPA sensor chip has been described earlier (Pui et al., *J. Endotoxin Research* 4:391–400 (1997)).

Injection of VtgCrFCES (800 ng/100 µl) resulted in a signal of ~2000 relative response units. This represents a ~92% saturation of lipid A which clearly indicates that VtgCrFCES binds to lipid A. Subsequently, injection of antibody (INDIA His-HRP Ab) against the poly-His tag of VtgCrFCES resulted in a further increase in the signal. The binding of INDIA His-HRP Ab further confirms that only VtgCrFCES was bound to the immobilized lipid A. The result also indicates that the six additional Vtgss-derived amino acids in the N-terminus of the protein do not interfere with the proper folding of the recombinant protein and its LPS-binding property. The properly folded VtgCrFCES is secreted. Injections of samples at various steps are marked on the sensogram. "Wash" indicates a washing step using pyrogen-free water. The relative response units of the signal are obtained by subtracting the response units recorded just before injection of sample from the response units recorded after injection of sample and a 2 min wash.

Figure 5A:
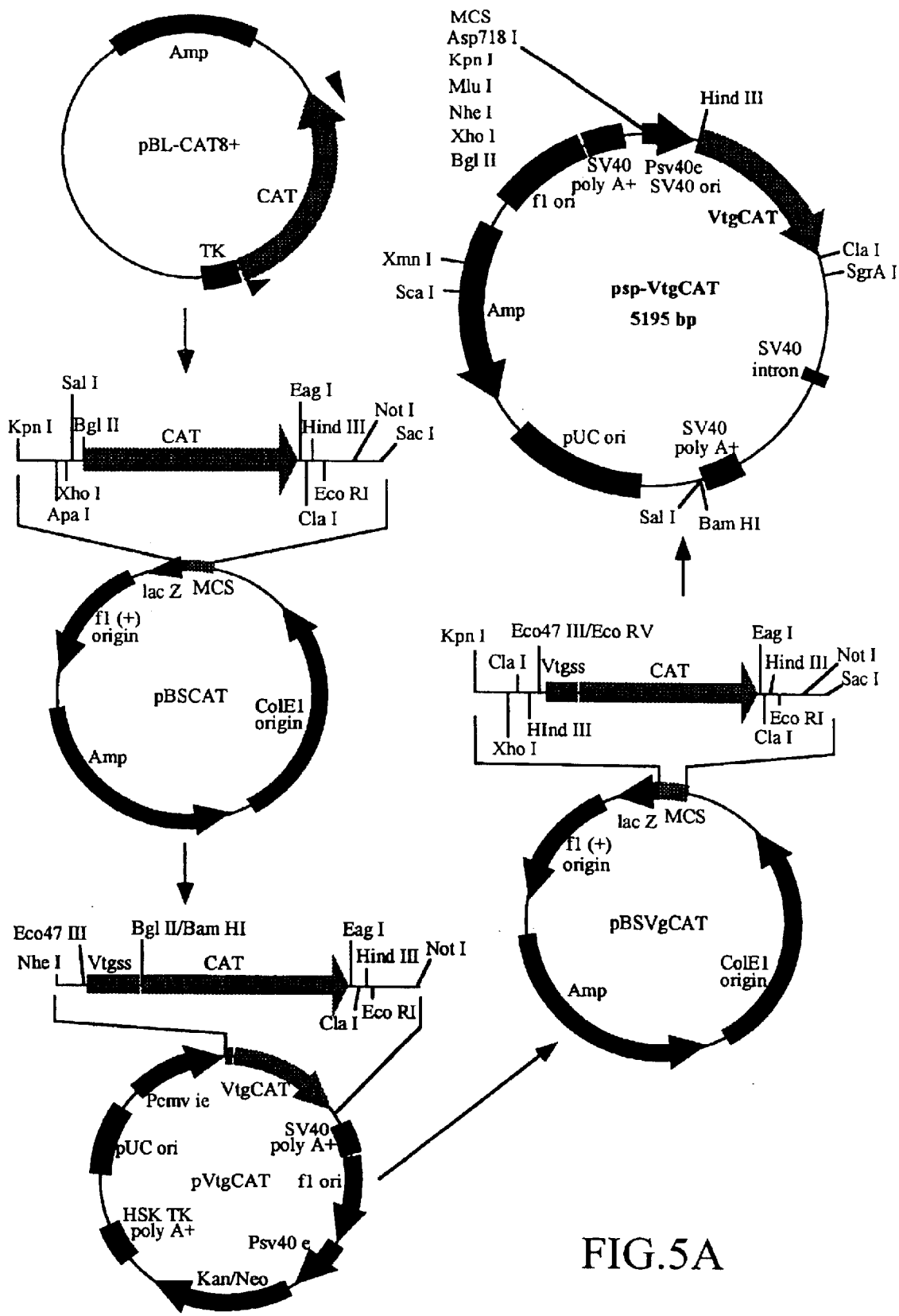

FIG. 5A shows the construction of psp-VtgCAT. The CAT gene was isolated by PCR. The start ATG codon of the CAT gene was changed to CTG to ensure translation initiation at Vtgss as indicated in bold in the sequence of the CAT forward primer (SEQ ID NO:1) (5'-GAA GAT CTG CTG GAG AAA AAA ATC ACT GG-3'). The stop codon of the CAT gene is indicated in bold in the CAT reverse primer (SEQ ID NO:2) (5'-GC ATC GGC CGT GCC TTA AAA AAA TTA CGC-3'). The temperature profile used includes a $1^{st}$ cycle (94° C./5 min; 50° C./1 min; 72° C./1 min), 29 cycles (94° C./45 sec; 50° C./30 sec; 72° C./30 sec) and final extension at 72° C. for 5 min. The PCR product of ~675 bp was purified using a Qiaquick™ PCR Purification Kit and subcloned into the HincII site of pBluescript™ II SK. The resultant construct is named pBSCAT. The CAT gene was released by BglII and NotI digestion and subcloned into compatible BamHI and NotI sites of pVtgEGFP. The CAT gene harboring Vtgss (VtgCAT) was subsequently released by using Eco47 III and NotI digest and recloned into the EcoRV and NotI sites of pBluescript™ II SK to form the vector pBSVtgCAT. This recloning step serves two purposes: (1) the sequences between Vtgss and CAT can be determined using a T7 primer; (2) this creates a HindIII site 5' of VtgCAT and a ClaI site 3' of VtgCAT for future subcloning into the pSEAP-Promoter vector.

FIG. 5B (SEQ ID NOS:14–17) shows the details of the Vtgss-CAT fusion in the pBSVtgCAT vector.

FIG. 5C shows the plasmid map of the pSEAP-Promoter vector.

FIG. 5D (SEQ ID NOS:14, 16–18) shows the amino acid and nucleotide sequences adjoining Vtgss and CAT in the vector psp-VtgCAT. The sequences between Vtgss and CAT were verified by Taqtrack™ sequencing (Promega) using a T7 primer. Both EcoRV/Eco47 III and BglII/BamHI sites were destroyed.

FIG. 5E shows the detailed plasmid map of psp-VtgCAT. The VtgCAT gene was subcloned downstream of the SV40 early promoter. The unique restriction enzymes in the multiple cloning site (MCS) were as illustrated. This construct can be used to analyze enhancer sequences cloned into any one of the unique sites in the vector.

Figure 5F:
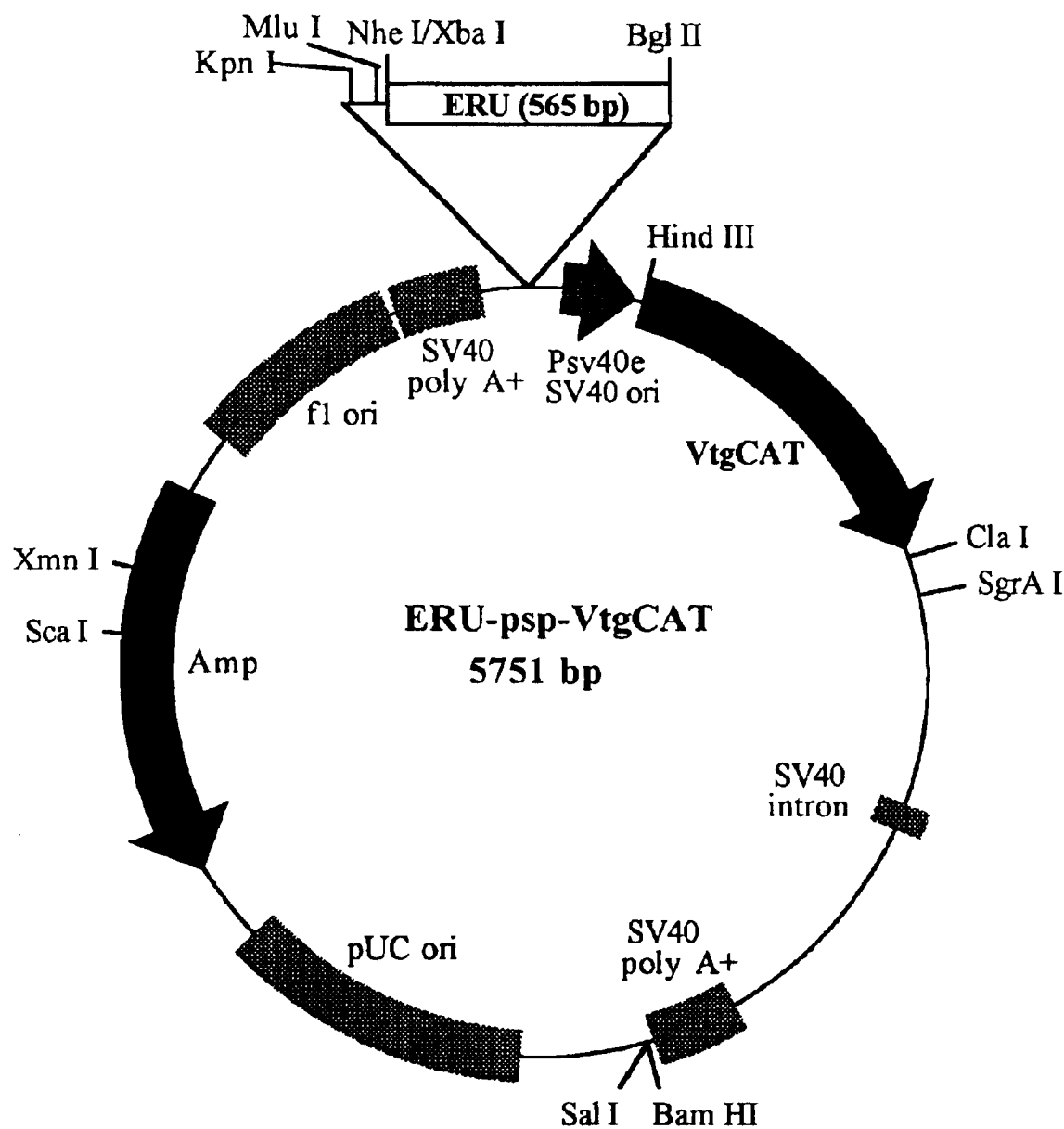

FIG. 5F shows the plasmid map of ERU-psp-VtgCAT. The estrogen response unit (ERU) of 565 bp from the Xenopus vitellogenin B1 gene was subcloned into the NheI and BglII site of psp-VtgCAT. The NheI/XbaI site was destroyed. The transcription of VtgCAT is under the influence of estrogen in this construct.

Figure 5G:
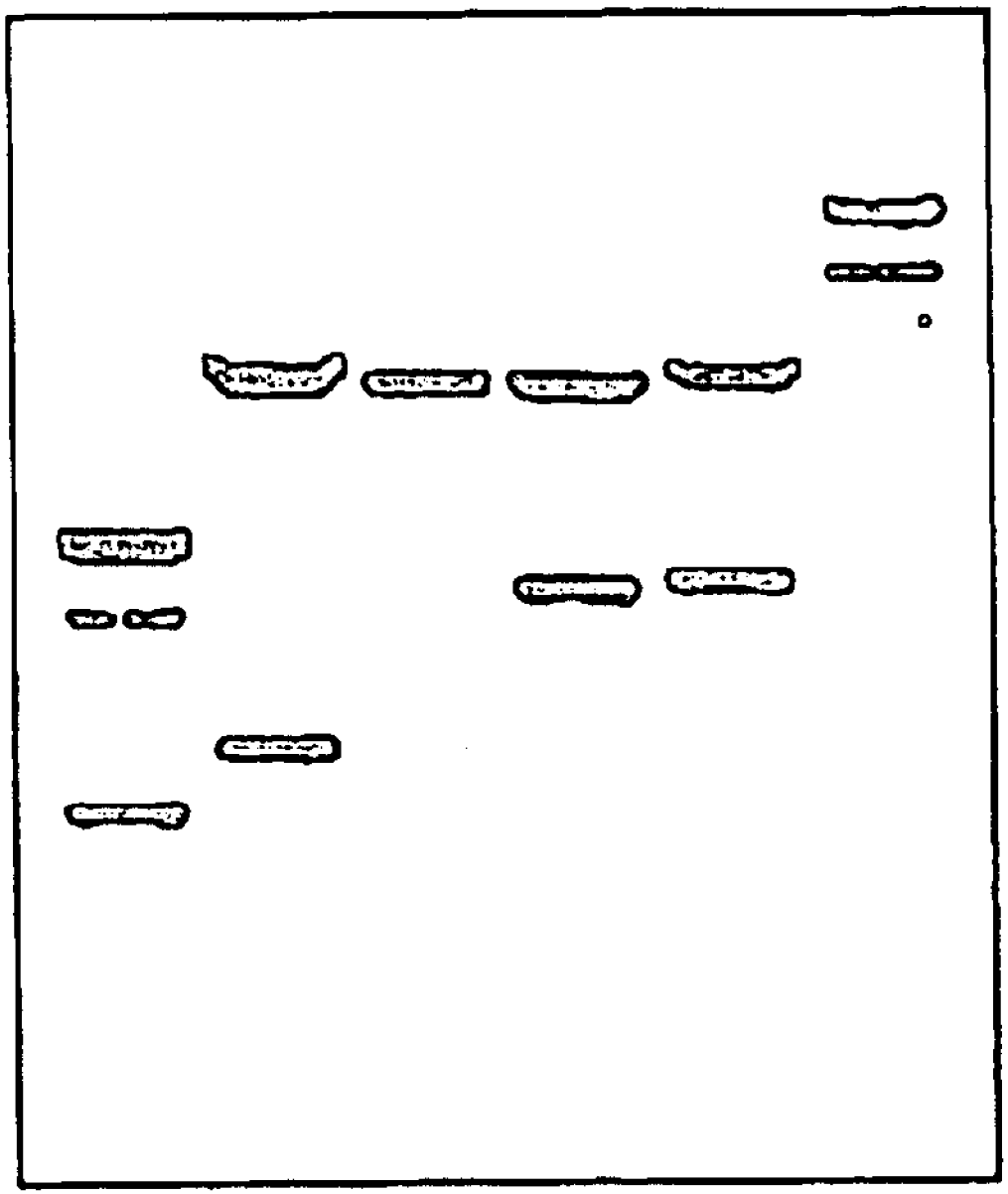

FIG. 5G shows restriction digests of various constructs.
Lane 1: 100 bp marker
Lane 2: ERU-psp-VtgCAT/HindIII and ClaI
Lane 3: psp-VtgCAT/HindIII and ClaI
Lane 4: pSEAP-Promoter/HindIII and ClaI
Lane 5: cER in pSG1/HindIII The VtgCAT (~830 bp) fragment can be released by Hind III and Cla digestion.

The upper band for ERU-psp VtgCAT is slightly larger than psp-VtgCAT because it contains a ~560 bp ERU.

Figure 6:
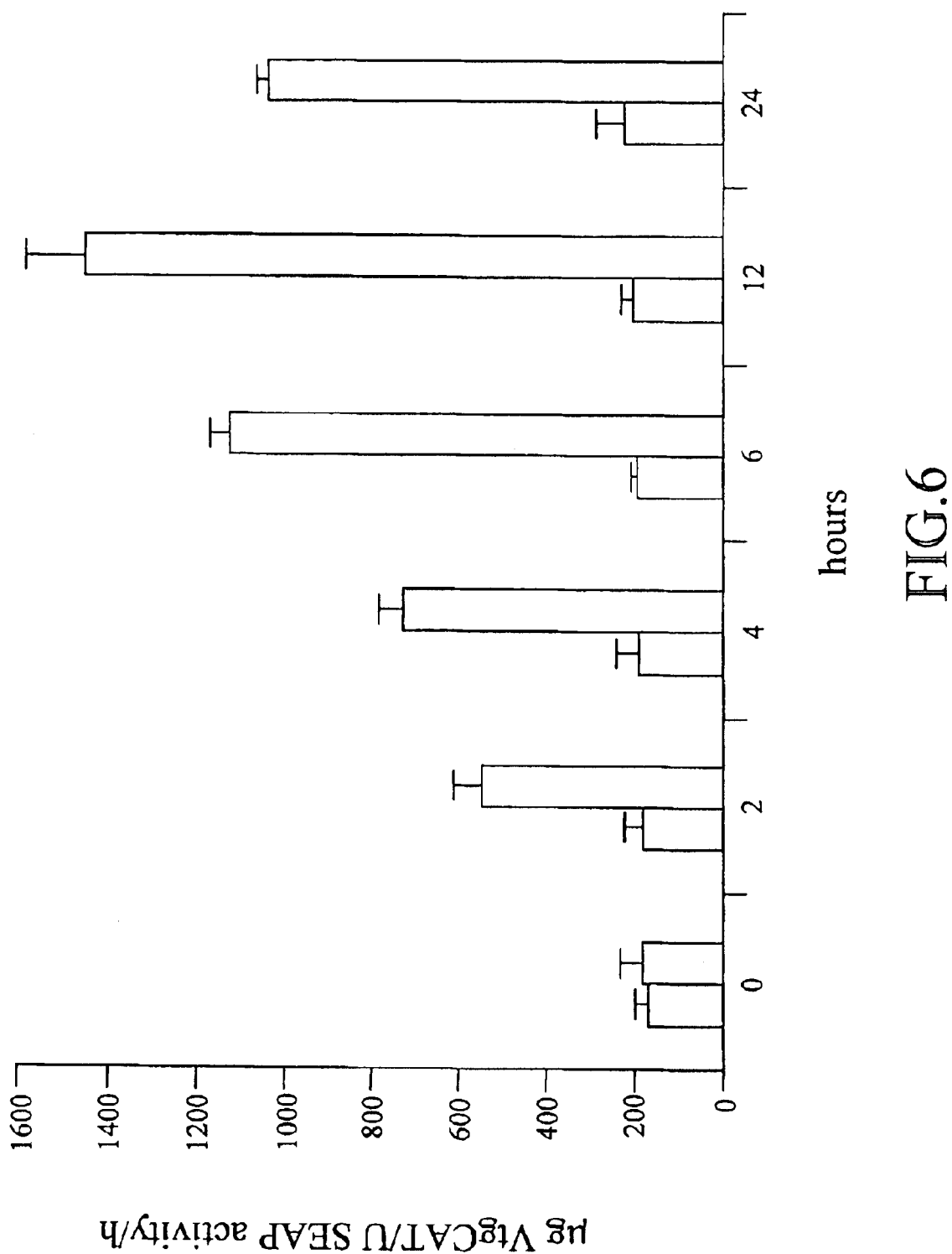

FIG. 6 shows the secreted VtgCAT expression profile over time in COS-1 cells. The COS-1 cells were cotransfected with ERU-psp-VtgCAT, pSG cER (chicken estrogen receptor expression vector) and pSEAP-Control in a ratio of 6:3:1. The result illustrates several important features. First, the recombinant VtgCAT was effectively secreted and accumulated in the culture medium. Second, the secretion of Vtg-CAT was not delayed. The uninduced cells (open box) exhibited only a marginal increase in VtgCAT over the period of 24 h. For induced cells (solid box), the increase in the production and secretion of VtgCAT can be detected as early as 2 h after the $E_2$-induction. A peak 7-fold increase (~1400 µg VtgCAT/U SEAP activity/h) in VtgCAT was observed 12 h post-induction as compared to the corresponding control. By 24 h, the VtgCAT decreased to ~1000 µg VtgCAT/U SEAP activity/h. The secreted VtgCAT was assayed using CAT ELISA (Boehringer Mannheim) SEAP was measured as described in Tan et al., *Mol. Cell. Endocrinol.* 123:146–161 (1996)). The VtgCAT amount was normalized using SEAP activity. $1 \times 10^{-8}$ M or estradiol was used for induction in all experiments.

Figure 7:
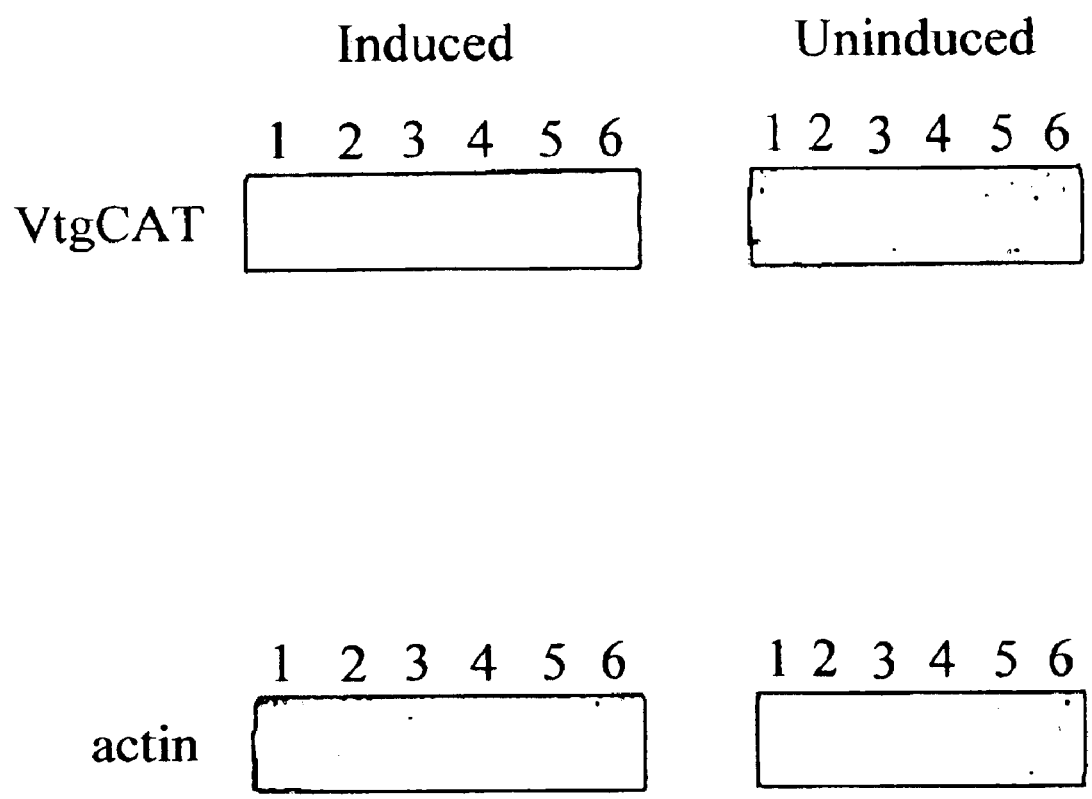

FIG. 7 shows a Northern blot analysis of $E_2$-induced VtgCAT expression for ERU-psp-VtgCAT. Total RNA was isolated from the COS-1 cells for $E_2$-induced and uninduced cells using RNAeasy™ Mini Kit (Qiagen). Ten µg of RNA was resolved on a 1.2% formaldehyde/agarose gel and alkaline transferred onto Hybond-N+™ membrane (Amersham). The membrane was probed initially with VtgCAT, stripped and reprobed with a mouse actin gene. The result indicates that the levels of VtgCAT in the culture medium are directly proportional to changes in intracellular concentration of VtgCAT mRNA. Thus, Vtgss can be utilized for reporter gene studies since there is no delay in its production and secretion. An actin cDNA probe was used to normalize the result.

Lane 1: 0 h
Lane 2: 2 h
Lane 3: 4 h
Lane 4: 6 h
Lane 5: 12 h
Lane 6: 24 h

Figure 8A:
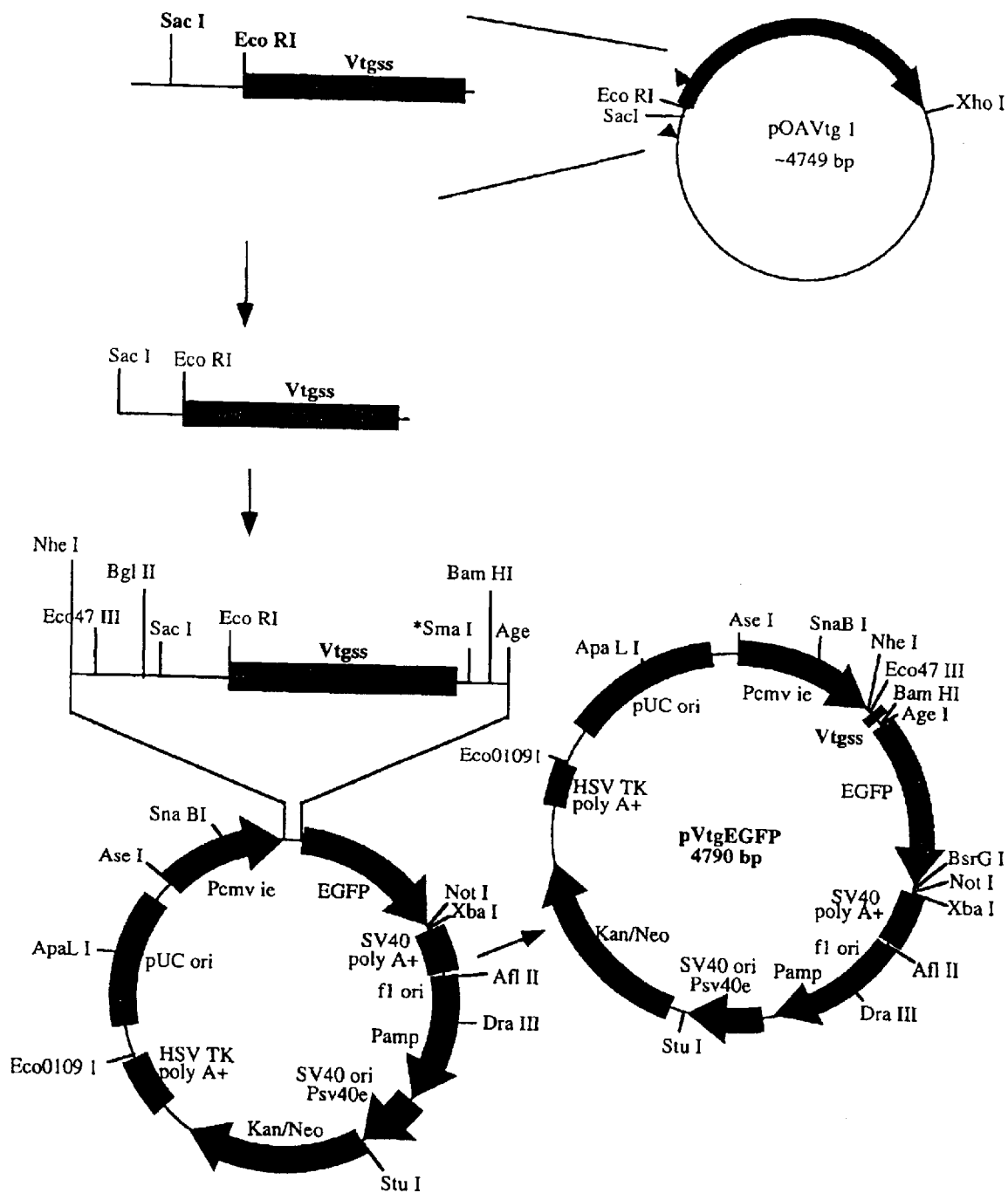

FIG. 8A shows the construction of pVtgEGFP. The Vtgss was isolated by PCR using a vector T3 primer and a OaVtgExon2 reverse primer (SEQ ID NO:3) (5'-CCAAGTTGGACTGGTCCCCCA-3') using pOaVtg 1 as a template. The PCR conditions used includes a $1^{st}$ cycle (94° C./5 min; 52° C./1 min; 72° C./1 min), 29 cycles (94° C./1 min; 52° C./30 sec; 72° C./30 sec) and final extension of 72° C. 5 min. The PCR product was purified using Qiaquick™ Nucleotide Purification Kit (Qiagen) and digested with SacI. This blunt-end (from the PCR) and SacI fragment was subcloned into the SmaI and SacI sites of pEGFP-N1 (Clontech). Consequently, the SmaI site of pEGFP-N1 was destroyed. To reduce the distance between the transcriptional start site and the promoter, the clone was digested with Eco RI and BglII, Klenow end-filled, and religated to give pVtgEGFP.

Figures 8B, 8C:
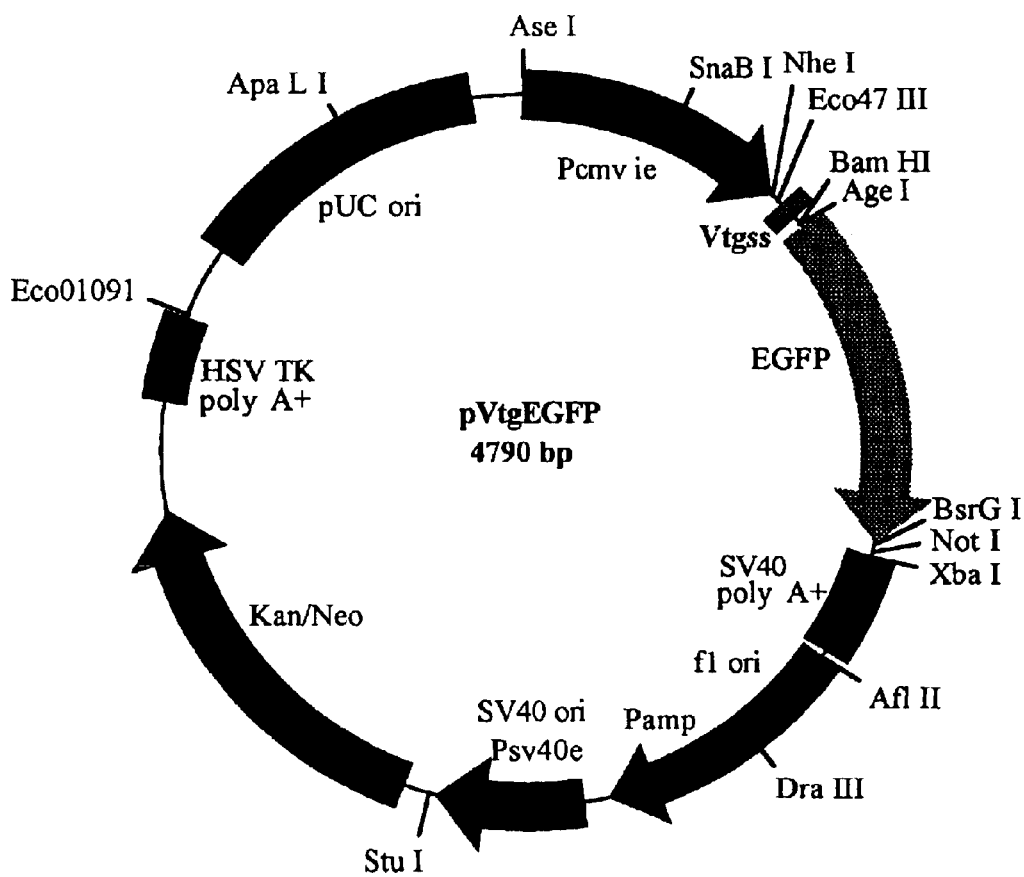

FIG. 8B (SEQ ID NOS:19–20) shows the details of the Vtg-EGFP fusion in the vector pVtgEGFP.

FIG. 8C shows the detailed plasmid map of pVtgEGFP. The VtgEGFP was subcloned downstream of the CMV promoter. Several unique sites flank both the Vtgss and EGFP to allow more flexibility in cloning. The sequence junction of Vtgss EGFP was determined using Taqtrack™ sequencing and an EGFP reverse primer (SEQ ID NO:4) (5'-CCCTCGCCGGACACGCTGA-3'). The transcriptional start site was determined by Teo et al. ("A Novel Piscine Vitellogenin Gene: Structural and Functional Analyses of Estrogen-Inducible Promoter", *J. Mol. Cell. Endocrin.* (1998), in press).

Figure 8D:
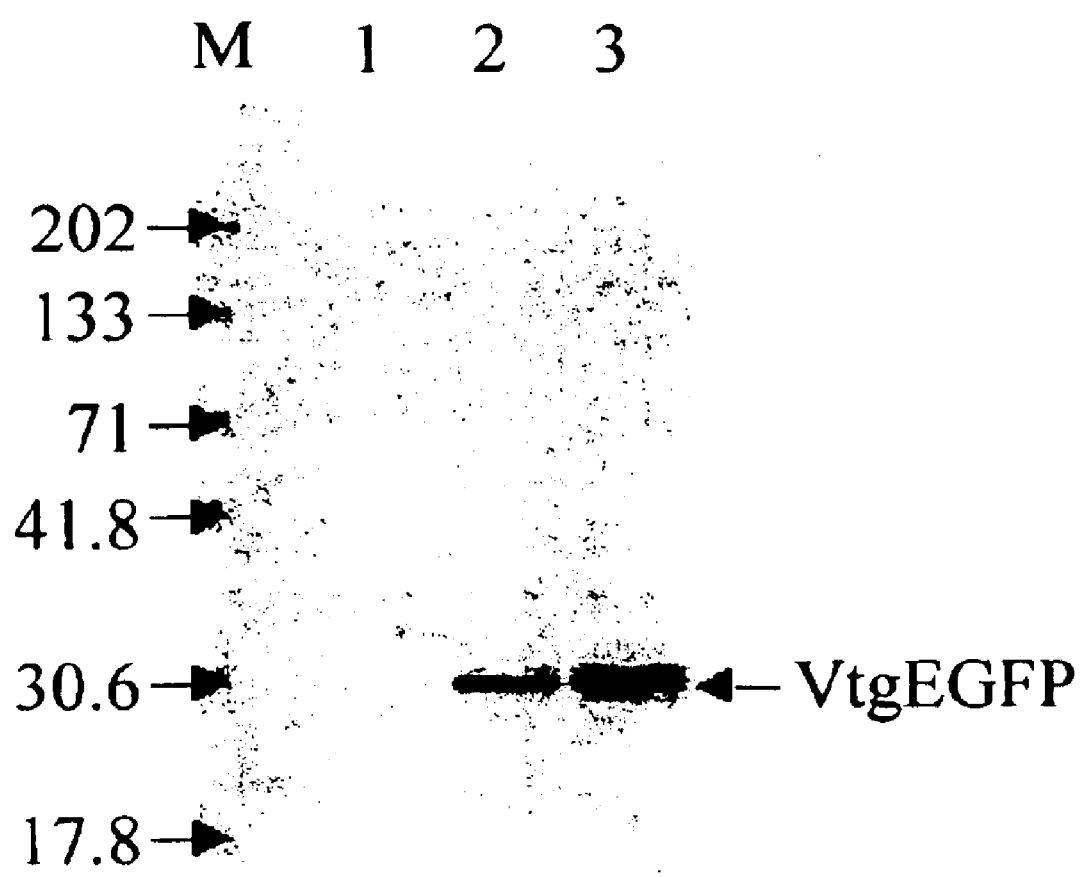

FIG. 8D shows western blot analysis of VtgEGFP expression in COS-1 cells. Transient transfection of COS-1 cells with pVtgEGFP was performed using Lipofectamine™ (Gibco). Forty-eight hours post transfection, both the medium and cell lysate were sampled. The result indicates that majority of VtgEGFP was secreted into the culture medium. A weaker immunoreactive band was also identified in the cell lysate using GFP antibodies. This is most likely due to the translation initiation at the start ATG codon of native EGFP. This shows that Vtgss can direct secretion of another reporter gene, EGFP. However, the optimal result for Vtgss-directed secretion can be achieved if the start codon of the EGFP gene is replaced or removed so that translation begins at the start codon of the Vtgss.

Lane M: Bio-Rad Kaleidoscope™ marker
Lane 1: control culture medium (24 h, 30 μg)
Lane 2: VtgEGFP culture medium (24 h, 30 μg)
Lane 3: VtgEGFP culture medium (48 h, 30 μg)

Figure 9:
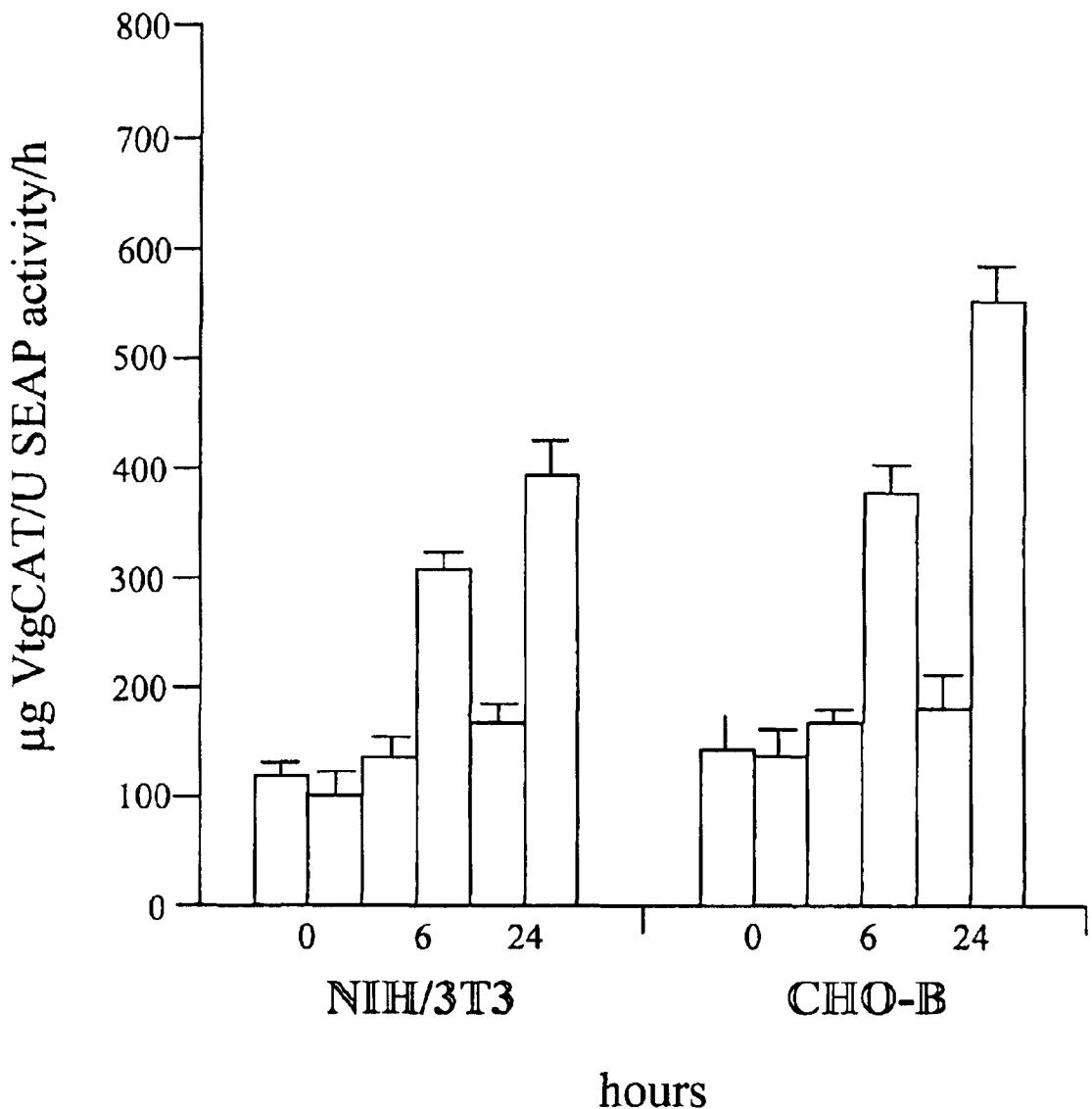

FIG. 9 shows the secreted VtgCAT expression profile over time in NIH/3T3 (normal mouse fibroblast) and CHO-B (Chinese hamster ovary) cells. NIH/3T3 and CHO-B cells were cotransfected with ERU-psp-VtgCAT, pSG cER (chicken estrogen receptor expression vector) and pSEAP-Control in a ratio of 6:3:1 using Lipofectamine™ (Gibco). The result shows that recombinant VtgCAT was effectively secreted and accumulated in the culture medium. Thus, secretion of VtgCAT was not limited to COS-1 cells; estrogen-induced expression of ERU-psp-VtgCAT can also be observed in other mammalian cells. The uninduced cells (open box) exhibited only a marginal increase in VtgCAT over the period of 24 h. For induced cells (solid box), the increase in the production and secretion of VtgCAT can be detected in the earliest indicated time point of 6 h after the $E_2$-induction. A peak showing 4-fold (~400 μg VtgCAT/U SEAP activity/h) and 5.5-fold (~550 μg VtgCAT/U SEAP activity/h) increase in VtgCAT were observed for NIH/3T3 and CHO-B cells, respectively. In contrast to COS-1, the lower level of induction is due to the lack of the large T-antigen which would otherwise amplify the signal. Importantly, the results indicate that the secretion of Vtg-CAT is not limited to a particular cell type. The secreted VtgCAT was assayed using CAT ELISA (Boehringer Mannheim). SEAP was measured as described by Tan et al. *Mol. Cell. Endocrinol.* 123:146–161 (1996)). The VtgCAT amount was normalized using SEAP activity.

Figure 10:
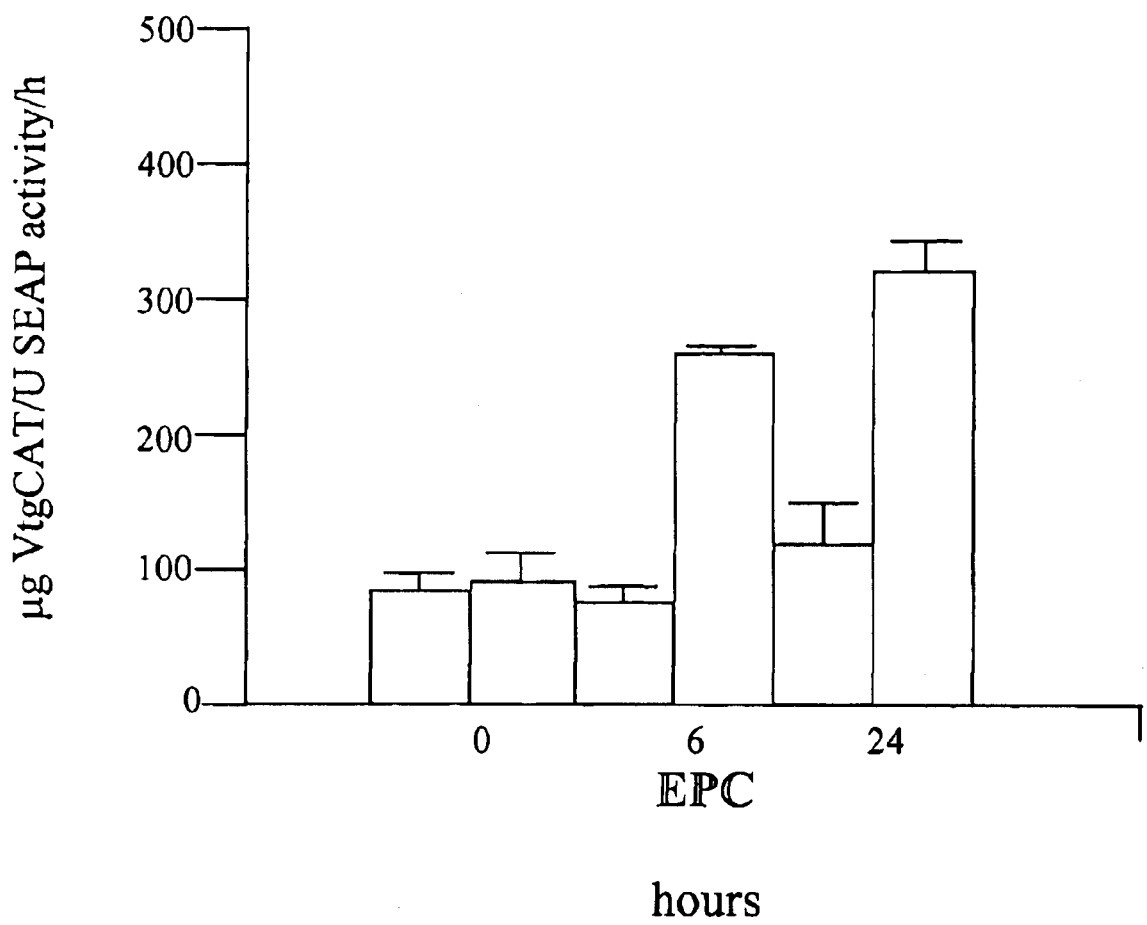

FIG. 10 shows the secreted VtgCAT expression profile over time in EPC (carp epithelial cells), a piscine cell line. (Open box, uninduced; solid box, estrogen-induced cultures.) A detectable amount of VtgCAT can be observed at 6 h. The EPC cells were cultured at a low temperature of 25° C. A 3-fold increase in VtgCAT can be detected by 24 h after estrogen-induction. The efficient production and secretion of VtgCAT was again demonstrated in this piscine cell line. The low metabolic rate of EPC would conceivably produce less VtgCAT, but this does not affect the secretion efficiency conferred by the SS of the invention. The secreted VtgCAT was assayed using CAT ELISA (Boehringer Mannheim). SEAP was measured as described in Tan et al., *Mol. Cell. Endocrinol.*, 123:146–161 (1996)). The VtgCAT amount was normalized using SEAP activity.

Figure 11:
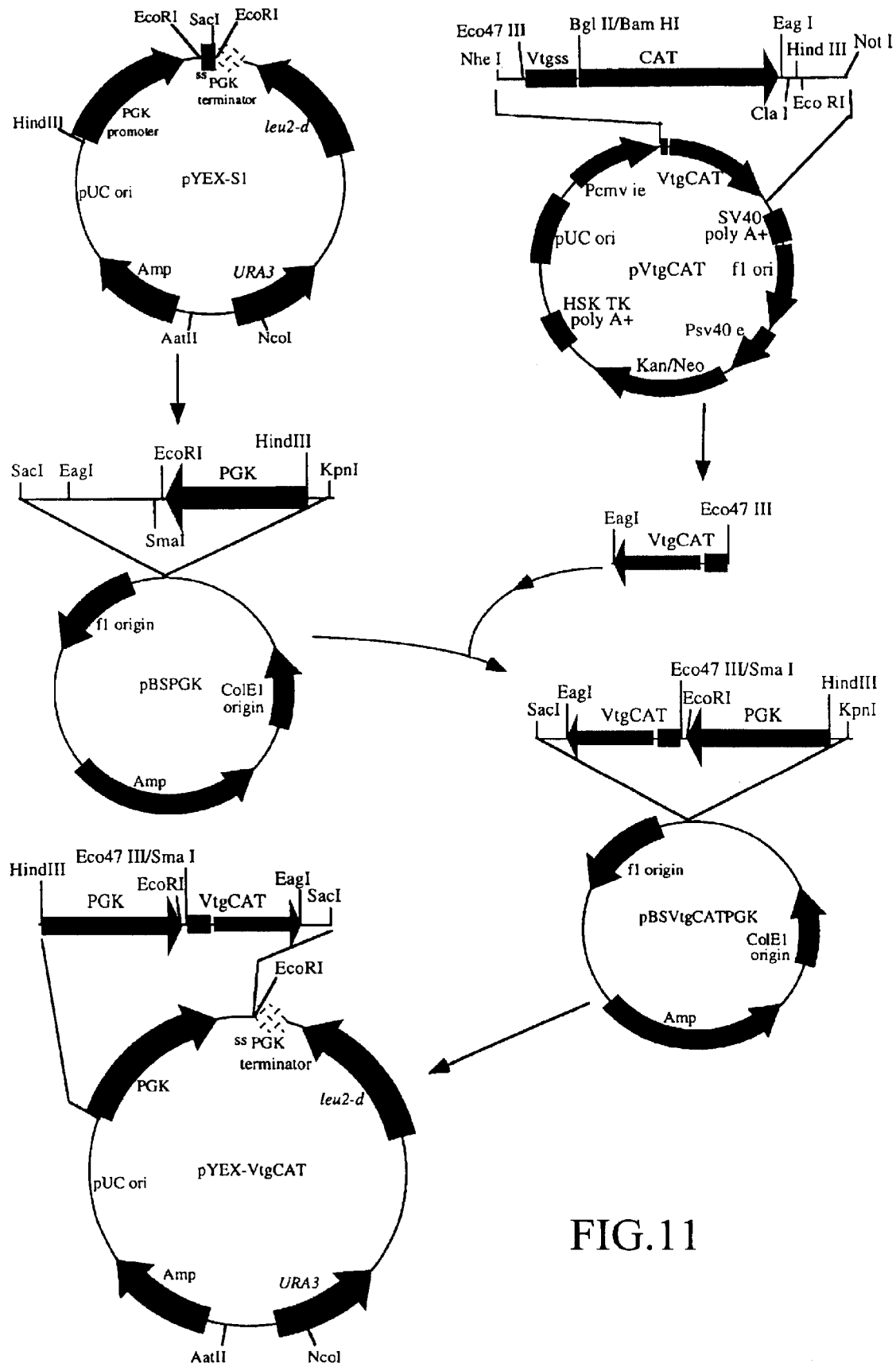

FIG. 11 shows the construction of pYEX-VtgCAT. The pYEX-VtgCAT vector basically used the backbone from pYEX-S1 (Clontech) except that the original *K. lactis* killer toxin signal sequence was replaced by Vtgss. Due to the limited number of cloning sites in the original pYEX-S1, an intermediate vector pBSPGK was constructed. pBSPGK consists of the PGK promoter, released via HindIII and Eco RI digestion from pYEX-S1, and subcloned into the corresponding sites of pBluescript™ II SK. This construct is a very useful intermediate as it provides more unique sites for cloning genes of interest. The VtgCAT fragment was released from pVtgCAT by Eco47 III and EagI digestion and subcloned into the SmaI and EagI sites of pBSPGK, respectively. The entire fragment harboring the PGK promoter and VtgCAT was released by HindIII and SacI digestion and subcloned into the similar site of pYEX-S1. Consequently, expression of pYEX-VtgCAT was driven by the strong constitutive PGK promoter and transcription terminated by the PGK terminator.

Figure 12:
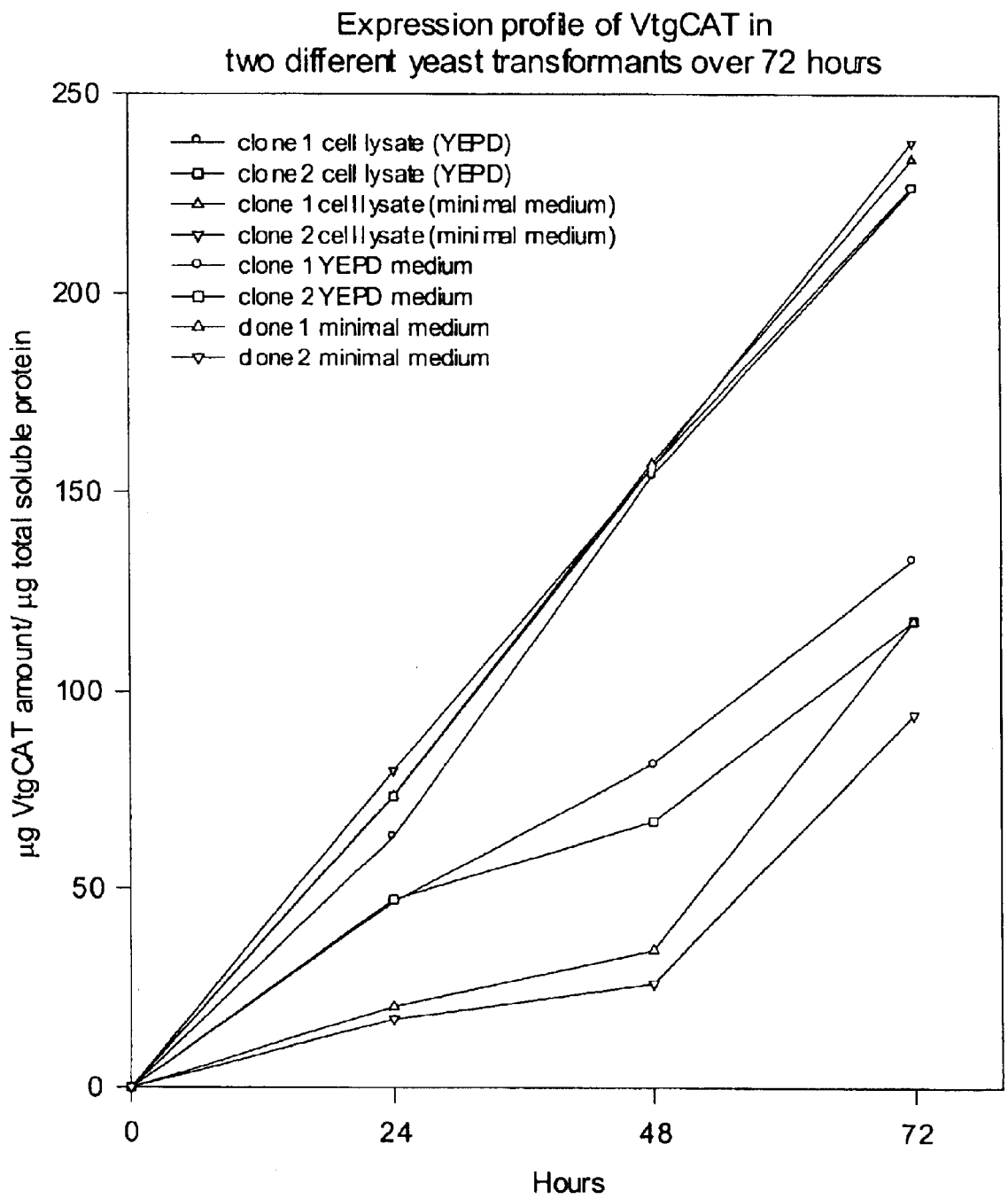

FIG. 12 shows the expression profile of VtgCAT in two different yeast transformants over 72 hours. The construct pYEX-VtgCAT was transformed into *S. cerevisiae* strain DY150 using the single-step transformation method described by Chen et al., *Curr. Genet.* 21:83–84 (1992)). The transformants were selected on synthetic minimal medium agar containing all the required supplements except uracil. 100 ml YEPD medium (pH 5.0) contained in a 500 ml baffled flask was inoculated with a single colony of pYEX-VtgCAT and grown for 16 h at 30° C. with vigorous shaking. Subsequently, 2×50 ml of the yeast were collected independently by centrifugation for 10 min at 800×g. One 50 ml pellet was resuspended in 200 ml YEPD medium and grown for 72 h at 30° C. with vigorous shaking in a 1 L baffled flask. The other 50 ml pellet was resuspended in 200 ml minimal medium (MM) and grown as above. At 24, 48, and 72 h, two ml aliquots of the culture were removed. The yeast and medium were separated by centrifugation. The cell lysate was obtained by lysing the yeast pellet (resuspended in phosphate buffered saline) with glass beads, while the culture medium was collected and frozen without any pretreatment. The pH of the culture was also monitored using appropriate universal pH indicator paper and adjusted to pH 5.0 using 1 M potassium phosphate buffer (pH 8.0). The amount of VtgCAT secreted into the culture medium and in the cell lysate were assayed using CAT ELISA (Boehringer Mannheim). Total soluble protein was used to normalize the data.

Figure 13:
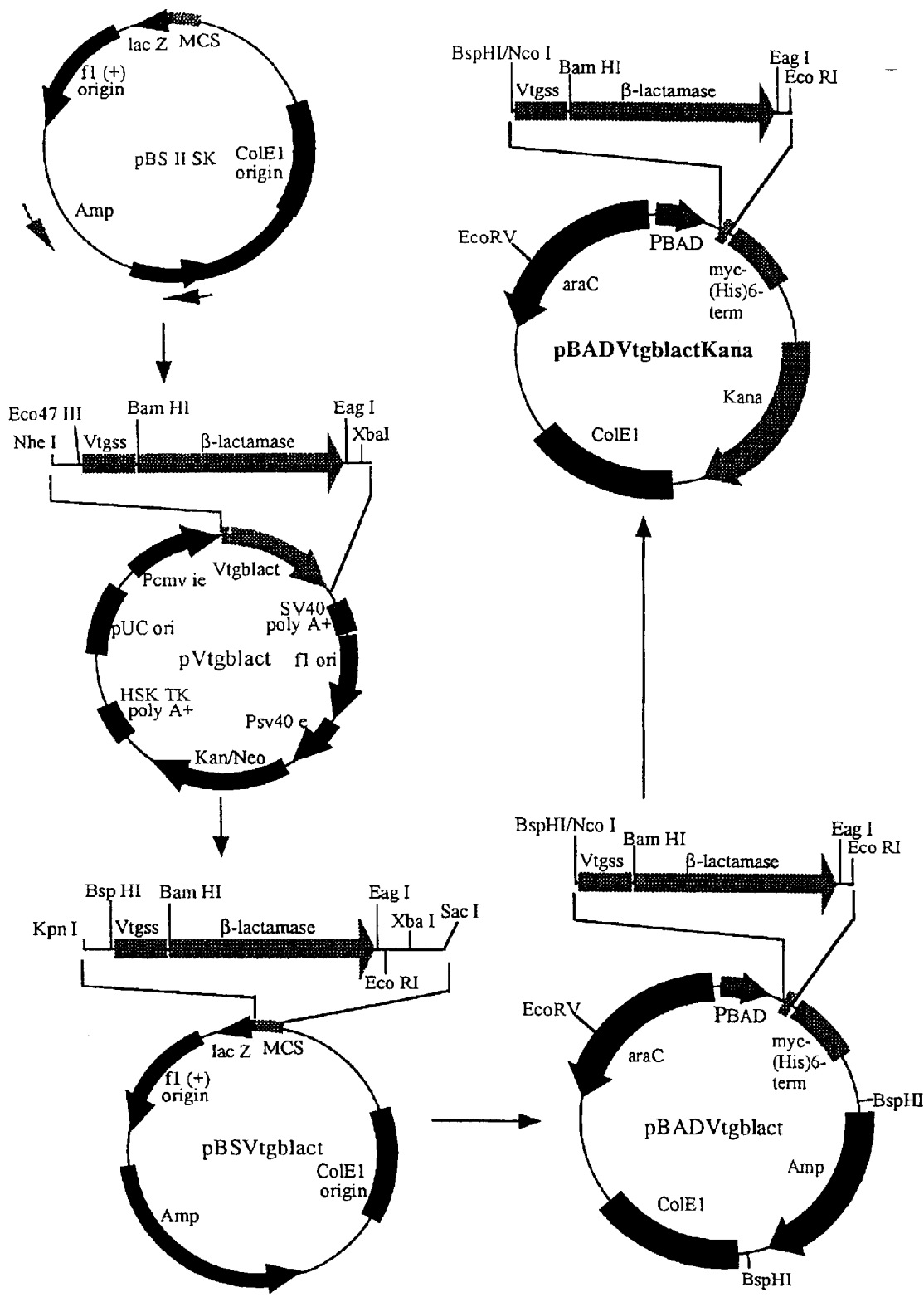

FIG. 13 shows the construction of pBADVtgblactKana. The β-lactamase gene was isolated by PCR using blactfor (SEQ ID NO:5) (5'-CCGGGATCCAGAAACGCTGGTGAAAGTAA-3') and blactrev (SEQ ID NO:6) (5'-GCGGCCGTTACCAATGCTTAATCAGTGAG-3') using pBluescript™ II SK as a template. The PCR primers were designed to exclude the native β-lactamase secretory signal. The PCR conditions used include a first cycle (94° C./45 sec; 50° C./30 sec; 72° C./1 min), 29 cycles (94° C./45 sec; 50° C./1 min; 72° C./30 sec) and final extension (72° C./5 min). The approximately 790 basepair PCR product was purified using a Qiaquick™ PCR Purification Kit (Qiagen) and digested with BamHI and EagI. This BamHI-EagI PCR fragment was subcloned into the BamHI and NotI sites of pVtgEGFP. To maintain optimal distance between the promoter and the ATG start codon, a second round of PCR was performed using BspSSFor (SEQ ID NO:7) (5'-GGGTCATGAGGGTGCTTGTACTAGCTCTT-3') and blactrev primers and using pVtgblact as template. The second PCR follows a thermal regime of a first cycle (94° C./5 min; 60° C./1 min; 72° C./1 min), 29 cycles (94° C./45 sec; 60° C./30 sec; 72° C./30 sec) and a final extension of 72° C./5 min. The resulting PCR fragment of about 865 basepairs was purified as above and cloned into Bluescript™ II SK. This Vtg-β-lactamase fragment was released by BspHI and EcoRI digestion and subsequently subcloned into the NcoI and EcoRI sites of pBAD/myc-His B. The vector's β-lactamase gene was released by BspHI digestion, and the vector ends were blunt-ended by Klenow enzyme. Then a kanamycin resistance gene obtained as a 2461 basepair DraI fragment from pGFP-N3 was inserted into the blunt-ended vector. The resulting plasmid, named pBADVtgblactKana was transformed into *E. coli.* LM194 competent cells.

FIG. 14A shows the amino acid (SEQ ID NO:22) and nucleotide (SEQ ID NO:21) sequences at the junction of Vtgss and β-lactamase in pBADVtgblactKana.

FIG. 14B shows the plasmid map of pBADVtgblactKana. The Vtg-β-lactamase gene was cloned downstream of the araBAD promoter (pBAD). The translation initiation site of Vtgss was constructed so that it is 9 basepairs from the optimized ribosome-binding site. The sequence junction of Vtg-β-lactamase was determined using Taqtrack™ sequencing. Both the BspHI site of Vtg-β-lactamase and NcoI site of the pBAD/myc-His B vector were destroyed.

Figure 15:
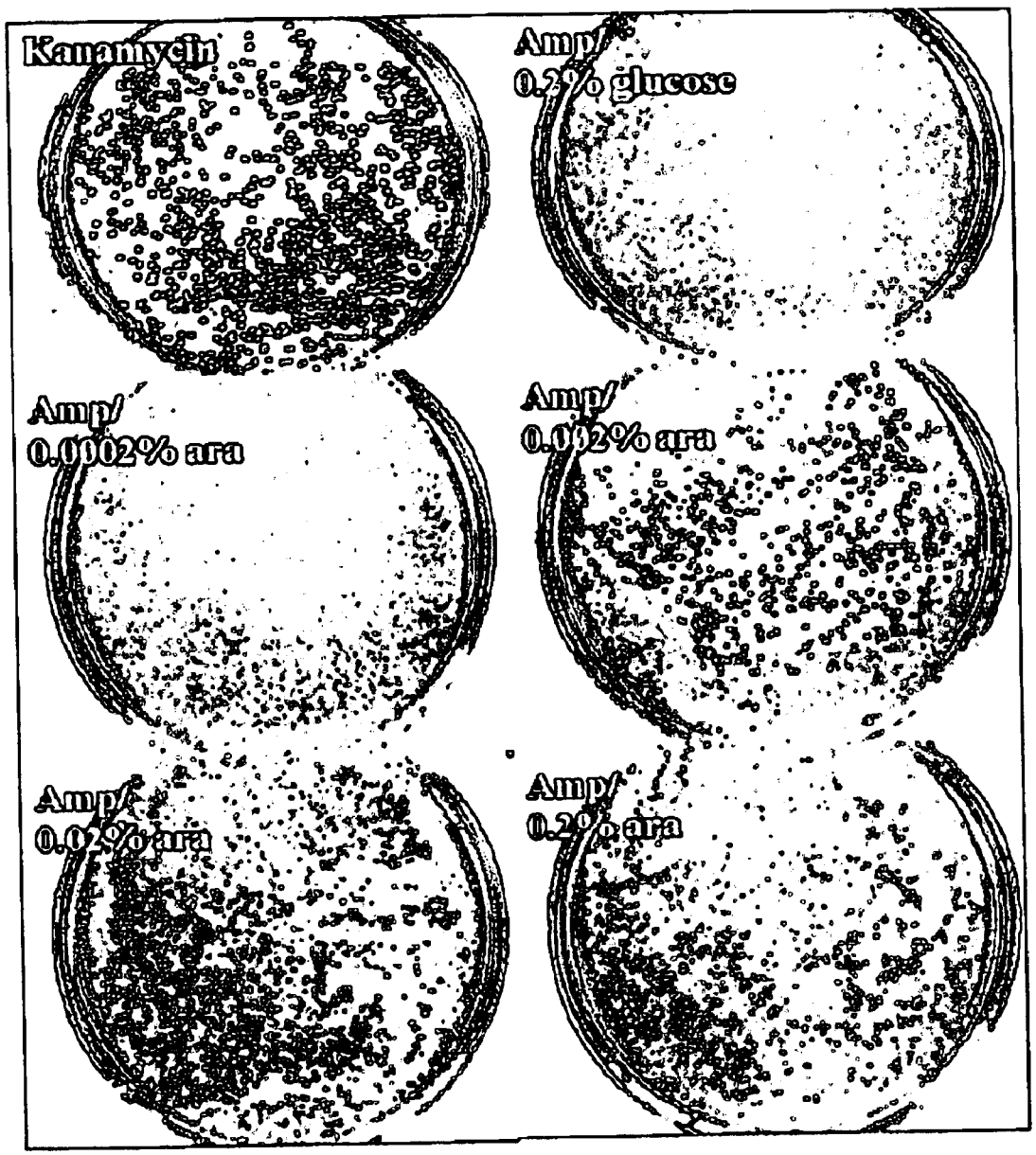

FIG. 15 shows a plating assay of Vtg-β-lactamase induction. In the absence of inducer or at very low levels of inducer (arabinose), no colonies are observed. Increasing amounts of inducer provides for survival of increasing numbers of colonies. Thus, when a selectable marker gene is used as a reporter gene, the plating assay provides an easy semi-quantitative assay for reporter gene activity.

Figure 16:
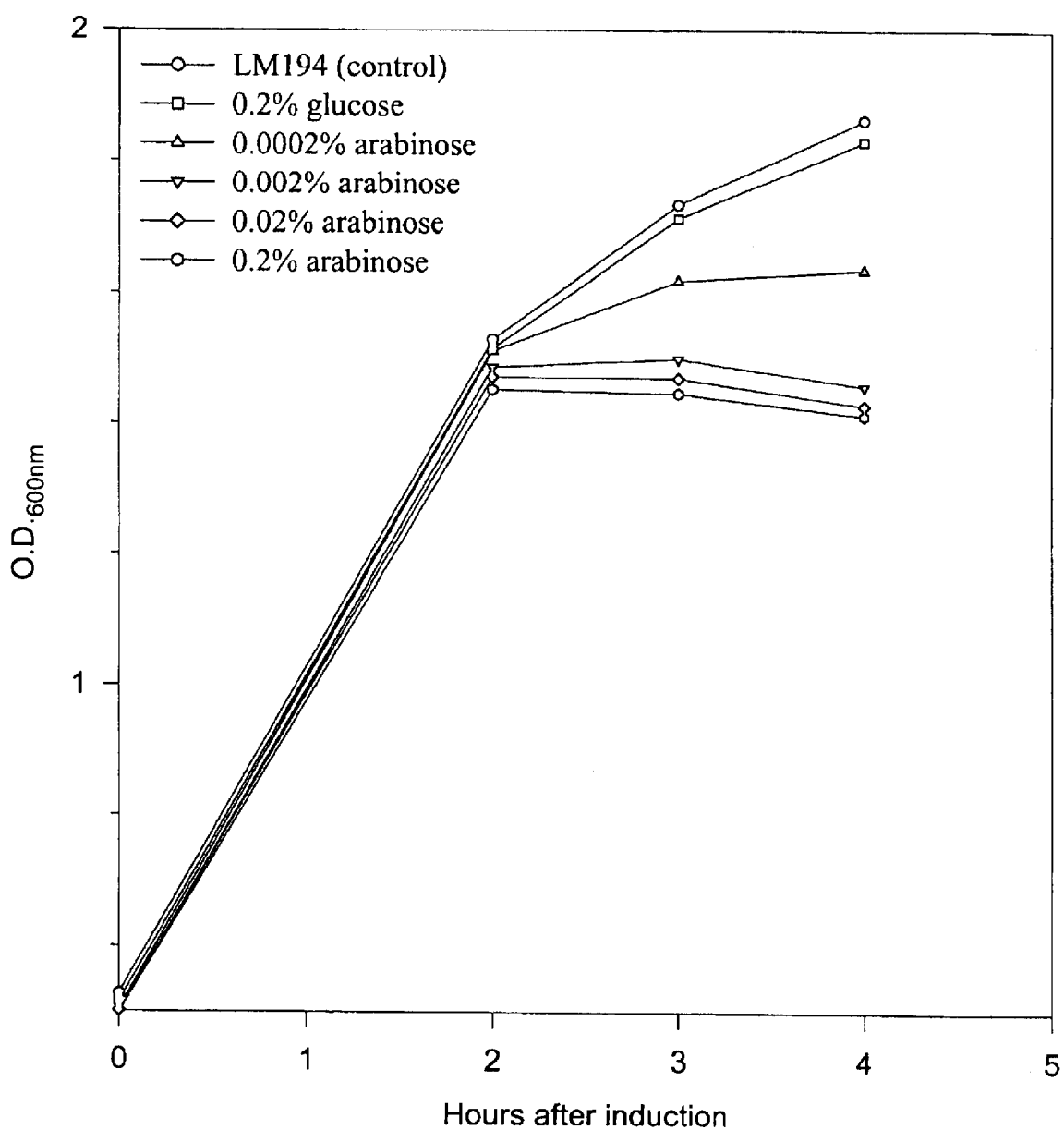

FIG. 16 shows the growth profile of the bacteria after induction with arabinose. The growth profile was monitored at $O.D._{600nm}$. It is clear from the graph that a pBADVtgblactKana clone grown in RM medium (■) with 0.2% glucose (i.e., no induction) exhibited a growth profile similar to the control LM194 host bacteria (●). Addition of arabinose, at various concentrations, affected the growth of the pBADVtgblactKana clone. Best growth is seen only when 0.0002% arabinose was used (▲). Higher concentrations of arabinose ($\geq 0.02\%$) resulted in a decrease in cell density. This is probably due to either (1) compromised growth of the cells due to overexpression of Vtg-β-lactamase or (2) toxicity due to a high level of Vtg-β-lactamase activity. The decrease in cell density has a pronounced effect on secretion of Btg-β-lactamase. The induction procedure was as described by the manufacturer (InVitrogen).

Figure 17:
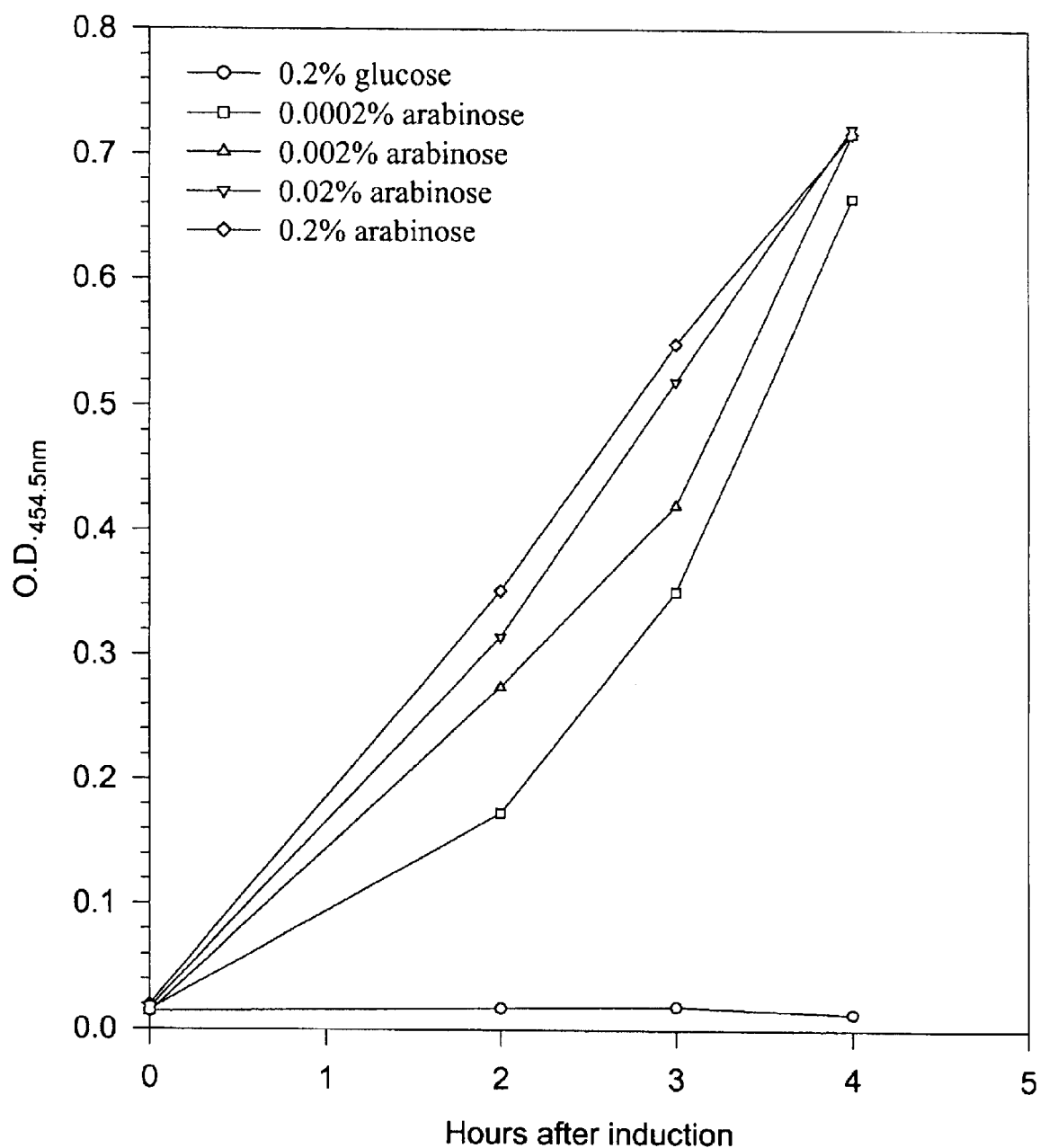

FIG. 17 shows the expression profile of Vtg-β-lactamase in the periplasmic space of bacteria. From the graph, no Vtg-β-lactamase was produced when a pBADVtgblactKana clone was cultured in RM medium with 0.2% glucose (●). This is expected since no inducer is added. Addition of arabinose resulted in expression and accumulation of Vtg-β-lactamase in the periplasmic space. The early expression profile is dose-dependent, with the highest expression observed when 0.2% arabinose was used (♦). However, by 4 h, this dose-dependent profile is not observed. This could be directly due to the growth retardation as seen in FIG. 15. Importantly, the recombinant Vtg-β-lactamase is functional and exhibited properties similar to native β-lactamase when measured using the standard calorimetric assay for β-lactamase (Cohenford et al., *Anal. Biochem.*, 168, 252–258 (1988)). The periplasmic space fraction was isolated as described by Laforet and Kendall (*J. Biol. Chem*., 266, 1326–1334 (1991)). The values obtained from the various time points for pBADVtgblactKana were subtracted from those of the corresponding LM194 controls.

FIG. 18 shows the expression profile of Vtg-β-lactamase in culture medium. From the graph, no Vtg-β-lactamase can be detected when a pBADVtgblactKana clone was grown in 0.2% glucose (●). Again, this is expected since no inducer is present. Surprisingly, Vtg-β-lactamase was detected in the culture medium, although not at as high a level as in the periplasmic space. But Vtg-β-lactamase in the culture medium was measured in the dilute medium. Even more surprising is that the Vtg-β-lactamase expression profile is reversed as compared with the Vtg-β-lactamase accumulation in the periplasm. The highest concentration of Vtg-β-lactamase was detected in the medium when the lowest concentration of 0.0002% arabinose was used in the culturing (■). Obviously, the ratio of induction and growth profile of bacteria are important factors. Rapid and high accumulation of. Vtg-β-lactamase in the periplasmic space does not translate into efficient secretion into the medium. Instead, low-level induction is preferred. The medium was clarified of bacteria by centrifugation at 4° C. for 10 min at 12,000 ×g. The filtered medium was kept in ice until all the1 samples were collected for assay.

FIG. 19 shows the cloning strategy of pVtg-Gal. The β-galactosidase coding sequences was PCR amplified using ForBamGal (SEQ ID NO:8) (5'-UCATGGATCCCGTGATTTCGTTGCCGGTCT-3') and RevEagGal (SEQ ID NO:9) (5'-GCCGGGCAGACATGGCCTGC-3') using pβgal-promoter (Clontech) as template. The PCR product was digest with BanHI and EagI and ligated into similar sites in pVtgblact. Using pBluescript II SK as an intermediate vector, a ~1.3 kb fragment harboring Vtgss and the 5' coding region of β-galactosidase was subcloned into pβgal-promoter at the HindIII and EcoRV sites. This vector expressing secreted β-galactosidase was designated pVtg-Gal.

FIG. 20 shows western blot analysis of Vtg-Gal using mouse anti-β-galactosidase. Fifty ug of medium was loaded and electrophoresed on a 10% SDS-PAGE gel. Lane 1: Day 5 medium; Lane 2: Day 4 medium; Lane 3: Day 3 medium; Lane 4: Day 2 medium; Lane 5: control medium; Lane 6: Blank; Lane 7: 20 ug of cell lysate from day 5 culture. The western blot was developed using Goat anti-mouse -HRP and Chemiluminescence Substrate.

FIG. 21 shows the rate of secretion of VtgCAT and Vtg-Gal in comparison with SEAP. COS-1 cells were transfected with 1 μg of Vtg-fusion construct: control vectors in a ratio of 8:2 by liposome-mediated transfection with 5–6 μl of Lipofectamine® reagent (Gibco-BRL) and incubated at 37° C. for 5 h as described by the manufacturer. After 36 h, the medium from cells of each time point was removed and replaced with 1 ml of fresh medium at an interval of 15 min over a period of 2 h. After the last time point, which should represent 0 min, an additional 1 h incubation was employed for all transfections to avoid low reading variations. At the end of incubation, the medium was retrieved and transferred to a microcentrifuge tube. Centrifugation was carried out as 12,000 ×g for 30 sec to pellet any detached cells present in the culture medium. 100 μl of supernatant was used for ELISA. SEAP was assayed using Great Escape™ SEAP Fluorescence Detection Kit (Clontech) as described by the manufacturer. Both SSCAT and SS-Gal were assayed using CAT ELISA and β-Gal ELISA (Boehringer Mannheim), respectively. For better comparison, the CAT ELISA and β-Gal ELISA were adapted for fluorescence using DIG Fluorescence Detection ELISA (Boehringer Mannheim). The procedures were as described by the manufacturer. SEAP was determined using a fluorimeter (Perkin Elmer) at $Ex_{360nm}$ and $EM_{449nm}$. VtgCAT and Vtg-Gal were detected at $Ex_{440nm}$ and $EM_{550nm}$.

DETAILED DESCRIPTION OF THE INVENTION

The present inventors have discovered that the portion of the amino acid sequence of vitellogenin that directs secretion of the protein from the cell can be linked to any other polypeptide and so direct secretion of that protein from a host cell. The secretory signal sequence of the invention, herein called "SS" or "Vtgss", is found in the amino-proximal portion of a vitellogenin protein.

A The preferred SS of the invention is obtained from a piscine vitellogenin protein, preferably from the fish *Oreochromis aureus*. There is a family of vitellogenin genes in this organism, which apparently comprises four subgroups of genes identifiable by different restriction maps of cloned cDNAs (J. L. Ding et al., *Biochem. Intl.* 20:843–852 (1990)). Melting of heteroduplexes formed between the cDNAs suggests that the overall nucleotide sequence variation among them is about 7%. The 5' end of the cDNAs show strong homology across all four subgroups by Southern blotting (B. H. Lee et al., *Biochem. Mol. Biol. Intl.* 34:75–83 (1994)). The most preferred SS of the invention is that having the amino acid sequence MRVLVLALAVALAVGDQSNLG (SEQ ID NO:10).

The sequence MRVLVLALAVALAVGDQSNLG (SEQ ID NO:10) can be modified by amino acid replacements and by insertions or deletions from the sequence. The SS may have additional individual amino acids or amino acid sequences inserted into the polypeptide in the middle thereof and/or at the N-terminal and/or C-terminal ends thereof so long as the SS retains the biological activities of directing secretion of a fusion protein from a eukaryotic cell and cleavage of the secretory signal sequence from the fusion protein at a site between the G and D residues, or between any amino acids substituted for these positions. Likewise, some of the amino acids may be deleted from the SS or substituted, so long as the resulting amino acid sequence retains those biological activities. Amino acid substitutions may also be made in the sequences so long as the polypeptide possesses the desired biological activities.

The secretion activity of the SS can be arranged assayed by measuring the proportion of a reporter protein secreted into the medium of cultured recombinant cells expressing SS-reporter protein fusions. The cleavage activity can be assessed by N-terminal sequencing of the secreted protein.

One or more amino acid residues within the sequence can be substituted with another amino acid of similar polarity which acts as a functional equivalent, resulting in an altered polypeptide that retains the desired biological activities. Amino acid substitutions are preferably "conservative amino acid substitutions". "Conservative amino acid substitutions" are substitutions of one amino acid by another amino acid wherein the charge and polarity of the two amino acids are not fundamentally different. Amino acids can be divided into the following four groups: (1) acidic amino acids, (2) neutral polar amino acids, (3) neutral non-polar amino acids and (4) basic amino acids. Conservative amino acid changes can be made by substituting one amino acid within a group by another amino acid within the same group. Representative amino acids within these groups include, but are not limited to, (1) acidic amino acids such as aspartic acid and glutamic acid, (2) neutral polar amino acids such as glycine, serine, threonine, cysteine, tyrosine, asparagine and glutamine, (3) neutral non-polar amino acids such as alanine, valine, leucine, isoleucine, proline, phenylalanine, tryptophan and methionine, and (4) basic amino acids such as lysine, arginine and histidine.

Proline is considered to be a less favored substituting amino acid with respect to the SS of the invention, due to its tendency to "break" alpha-helical secondary structure of peptides. Also, it is preferable to retain a basic amino acid, preferably lysine or arginine, at the second residue of the SS. Also, it is preferred that the G and D residues constituting the cleavage site in the SS be retained; any substitution of these two amino acids is preferably A or V for the G and E for the D.

Any integral number of additions or deletions of amino acids between 0 and 4 can be made to the SS; preferably only 1 or 2 additions or deletions are made. It is preferred that the stretch of hydrophobic amino acids in the interior of the SS be kept in the range 10–15 amino acids long, preferably 11–14, most preferably 11, 12 or 13 amino acids long.

The number of substitutions that is tolerated is larger. An important aspect of the SS is that the hydrophobic stretch in its interior portion be retained. Many of the non-polar amino acids in this portion can be substituted with other non-polar amino acids, especially those having hydrocarbon side chains, without affecting the activity of the SS. Preferably fewer than 7 of the amino acids in the SS, more preferably fewer than 3, are substituted overall.

The DNA encoding the SS of the invention can of course vary with respect to degeneracy of the genetic code. A preferred nucleotide sequence encoding the SS of the invention is nucleotides 18 through 80 of SEQ ID NO: 11. Also, in embodiments of the invention wherein DNA encoding a SS of the invention is joined to DNA encoding a desired protein to be expressed, the joining should be done so that the reading frame of the SS and of the desired protein are the same. The joining can be performed so that the 3' end of the DNA encoding the SS is joined directly to the 5' end of the DNA encoding the desired protein. Alternatively, the 3' end of the DNA encoding the SS can be joined to a "linker" DNA that encodes additional amino acids, which linker DNA is then joined also to the 5' end of the DNA encoding the desired protein.

In some embodiments of the invention, the desired protein is a "reporter protein" that has an easily assayed biological activity. The biological activity of the reporter protein is preferably closely correlated with the amount of the transcript encoding the reporter protein present in the cell, and in the most preferred embodiment, reflects the transcription activity of the promoter driving expression of the reporter protein. Examples of reporter proteins for which cloned DNAs and quantitative assays are known are chloramphenicol aminotransferase, green fluorescent protein or another aequorin, β-amylase, β-lactamase, luciferase, glucuronidase, alkaline phosphatase and β-galactosidase.

A biosensor can be made by making a construct comprising the SS and a desired protein operatively linked to a promoter sensitive to a particular chemical compound. "Operative linkage" of the promoter occurs where the transcription of the SS-desired protein cassette is driven by the promoter in the fashion normal for the promoter. Thus, if the promoter is a constitutive one, then transcription is constant. If the promoter is chemically-inducible or suppressible, then the transcription of the SS-desired protein cassette is similarly chemically-inducible or suppressible.

To complete the biosensor, a cell that intracellularly expresses or bears on its surface a receptor for the compound being sensed is transformed with the construct comprising the relevant promoter operatively linked to the SS-desired protein cassette. The cell surface receptor is preferably one that is endogenous to the cell, since then one can presume that the additional proteins required for transduction of the compound binding signal to the nucleus are present in the cell. In instances where the cell surface receptor is introduced by recombinant DNA methods, then the practitioner of ordinary skill will understand that a host cell that harbors the relevant signal transduction proteins should be used.

Cells bearing receptors for estrogen and estrogen-like compounds ("estrogen mimics") are preferred cells for creating biosensors of the invention. The estrogen signal transduction pathway is among the better understood ones, and several cell types that support estrogen-induced transcription of exogenous genes introduced by transformation are known (Tan et al., "Temperature-Dependence of Estrogen Binding: Importance of a Subzone in the Ligand Binding Domain of a Novel Piscine Estrogen Receptor"; Dana et al., "Novel Estrogen Response Elements Identified by Genetic Selection in Yeast are Differentially Responsive to Estrogens and Antiestrogens in Mammalian Cells"). Also, several cloned estrogen-responsive elements ("EREs") are known in the art (see, for example, N. S. Tan et al., Mol. Cell. Endocrinol. 123:149–161 (1996)).

The biosensors according to the invention allow easy assay for the presence of the relevant compound in a sample. The assay is performed by culturing cells constituting the biosensor in a medium. A sample of the medium is taken and assayed for the activity of the reporter protein encoded by the cassette to obtain a baseline level. Then the sample is introduced into the culture medium and the culture is continued. The medium is again sampled and the activity of the reporter gene measured. Changes in the activity of the reporter gene will reflect the presence of the relevant compound in the sample. Of course, alternate embodiments, such as separate, matched cultures of the biosensor cells in the presence and absence of the sample, can be envisioned. The particular media used are of course dictated by the cells used to construct the biosensor; media and methods of cell culture are generally known in the art.

In a similar manner, the SS of the invention can be used to make expression cassettes for any desired protein. The protein will be secreted into the medium of the culture. Use of serum-free culture media provides conditions where it is possible that the desired protein will be one of only a few, and possibly the only, polypeptide present in the culture medium. This greatly simplifies purification of the desired protein.

In other embodiments of the intention, it is desirable to produce a lipopolysaccharide-binding protein, such as Factor C of a horseshoe crab. Cloned cDNAs encoding Factor C from at least two species of horseshoe crab are known (see, U.S. Pat. No. 5,716,834 and Muta et al., J. Biol. Chem. 266:6554–6561,(1991)). The lipopolysaccharide-binding protein produced by the present invention can be used in the ways described in U.S. Pat. Nos. 5,712,144, 5,716,834, and 5,858,706. In those embodiments of the invention directed to production of a protein for quantitative assay or purification, it is most desired that cells that do not secrete proteases are used. Preferred host cells are COS, CHO, NIH/3T3, Drosophila cells, especially Schneider 2 cells, piscine epithelial cells (EPC) and yeast cells, such as S. cerevisiae and S. pombe and Pichia spp., especially protease-deficient yeast cells.

The present invention can also be used in an assay for heterologous gene expression. In this embodiment of the invention, cells are transformed with a vector that directs the expression of the heterologous protein to be expressed. The nucleic acid encoding the heterologous protein is joined to nucleic acid encoding the SS, thereby obtaining secretion of the expressed protein into the medium upon culture of the host cells. The presence of the heterologous protein in the culture medium can then be detected, for example by assay for its biological activity, if such is known, or by an immunologic method, if an antibody that specifically binds the heterologous gene product is available. Preferred methods for immunologic detection are ELISA (in any of the various known formats) and Western blotting. Labels for detection of antibody binding are not limiting of the method, but preferably the antibody is fluorescently labeled or enzymatically labeled.

The SS of the invention can also be applied to "enhancer trap"-type vectors, wherein a promoterless vector carrying a reporter gene is transformed into a cell, where it integrates at a random point in the genome in such a fashion that integration near a promoter results in expression of the reporter gene. In this embodiment, the reporter gene is made to incorporate the SS, thus expression of the reporter gene will result in secretion of the reporter protein out of the cell into the culture medium, thus simplifying screening for insertion in the vicinity of a promoter.

The SS of the invention can also be applied to expression of genes in chimeric or transgenic animals, to obtain secretion of a desired protein, especially of a therapeutic protein, into an extracellular compartment. In some embodiments, this method provides general dissemination of the protein throughout the animal. In preferred embodiments, the protein is secreted into extracellular matrix, which can thus result in local dissemination if the half-life of the protein is short or if it is made to bind to receptors on the surface of cells or to receptors in the matrix. Secretion into the extracellular matrix can also provide quite extensive dissemination if the protein has a long half-life and is able to diffuse through the matrix.

In other preferred embodiments, the protein is made to be secreted into the bloodstream, the lymphatic system or into the ducts of the breasts for secretion in milk by transformation of the appropriate cells.

EXAMPLE 1

Figure 1:
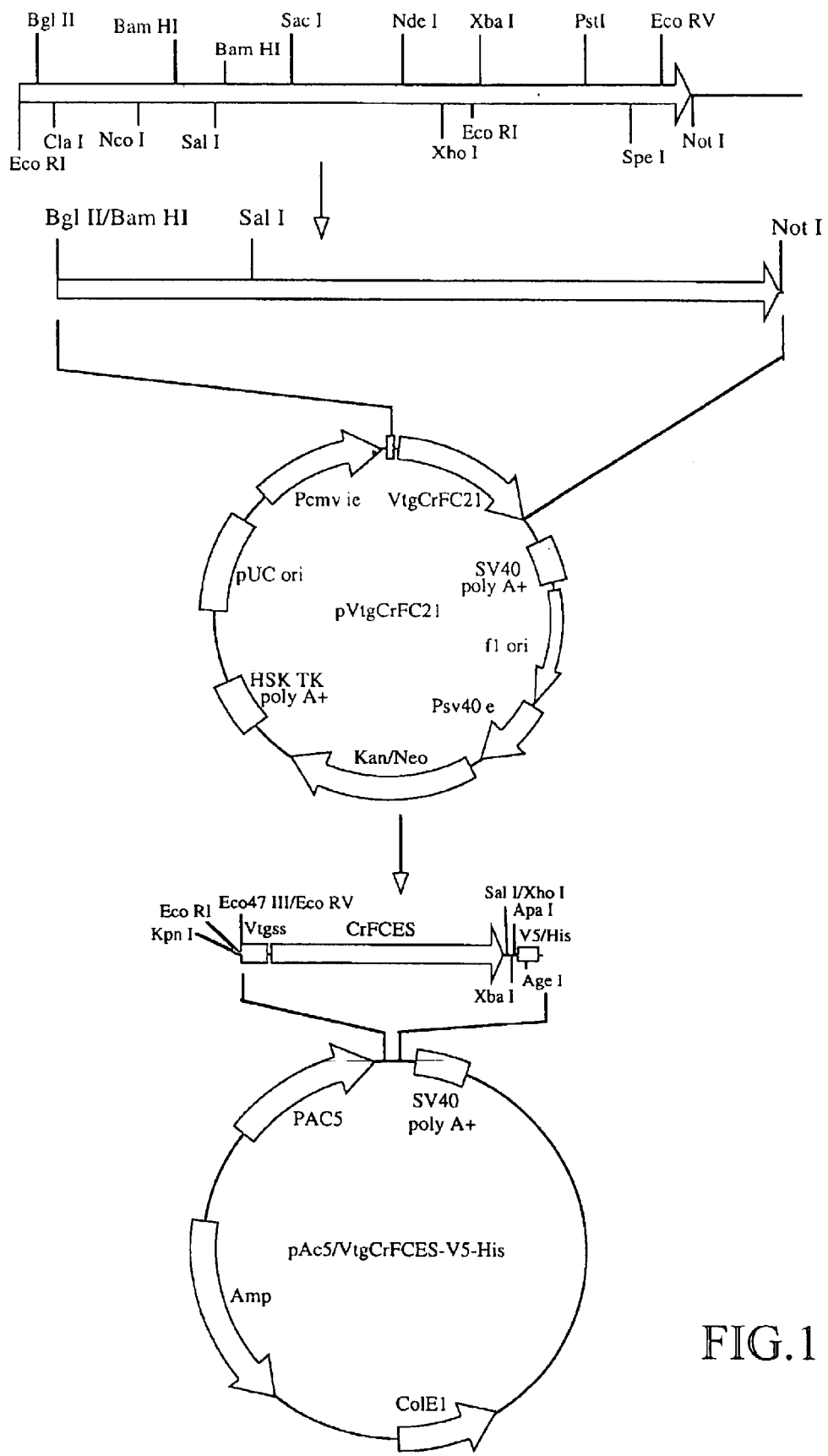
FIG. 1 shows the construction of pAc5/VtgCrFCES-V5-His. The full-length CrFC21 cDNA encoding Factor C was released by a BglII and NotI double digest. The released fragment was subcloned into the BamHI and NotI sites of VtgEGFP. Consequently, the BglII/BamHI site is destroyed. Then the LPS-binding domain of CrFC21 was released by digestion with Eco47 III and SalI (cutting an internal site). The fragment was subcloned into the EcoRV and XhoI sites of pAc5/V5-HisA to give pAc5/VtgCrFCES-V5-His. Both Eco47 III/EcoRV and SalI/XhoI sites are destroyed.

Cloning of Vtgss in LPS-binding Domain of CrFC Gene (CrFCES) for Expression and Secretion of Recombinant ES Protein From Drosophila Cells The O. aureus vitellogenin gene secretory signal (Vtgss) was fused upstream to the EcoRI-SalI cDNA fragment encoding the LPS-binding domain of Carcinoscorpius rotundicauda Factor C CrFCES (Ding et al., 1995. Mol. Marine Biol. & Biotechnology 44:90–103). The construct was inserted into the pAc5/V5-His vector backbone (InVitrogen, see FIG. 1).

Vitellogenin is the yolk protein of the oviparous and ovoviviparous animals. It is exclusively synthesized in the liver, secreted and finally deposited in the eggs. The secretion of vitellogenin is directed by its secretory signal. The expression of the LPS-binding domain of Factor C (~333 amino acids) is challenging because it is rich in $Ad^9$ cysteine residues and requires the correct formation of 9 disulfide bonds for full biological activity. The recombinant protein (VtgssCrFCES) is synthesized using the Drosophila Expression System™ (InVitrogen). Stable recombinant Drosophila cell lines were obtained and the distribution of the protein was identified by Western blotting using chemiluminescent detection. The recombinant protein was also purified to homogeneity for N-terminal amino acid sequencing.

Homogeneous cleavage between Vtgss and the adjoining mature CrFCES protein was demonstrated by N-terminal amino acid sequencing of VtgCrFCES. The data show that Vtgss is cleaved at a single point (FIG. 2). The absence of multiple cleavages shows that Vtgss directs homogenous production of secreted heterologous protein.

The Western Blot shows that practically all of VtgCr-FCES is secreted into the culture medium (FIG. 3). No intracellular VtgCrFCES was detected using chemiluminescent detection, which is very sensitive. The fusion of Vtgss to the LPS-binding domain resulted in its secretion whereas the native secretory signal of Factor C targets the LPS-binding domain intracellularly. The presence of VtgCrFCES in the culture medium allows simple purification from either batch or continuous culture.

The LPS-binding properties of the secreted protein are retained as shown by plasmon resonance studies, using the BIACORE™ in vivo biosensor apparatus (FIG. 4). This is despite addition of 6 Vtgss-derived amino acids to the N-terminus of the CrFcES protein. Thus Vtgss is capable of driving the secretion of correctly-folded CrFCES. Functional Vtgss truncated after the aspartic acid residue that is the carboxy side of the cleavage site (see, e.g., FIG. 8A) can be used to reduce the number of extra amino-terminal residues.

The expression vector employed here contains the basic features necessary for expression of recombinant proteins in heterologous cells; (1) an efficient promoter for transcription initiation; (2) enhancer elements for high level transcription; (3) mRNA processing signals such as mRNA cleavage and polyadenylation signals; (4) a polylinker containing multiple restriction endonucleases sites for insertion of foreign DNA; (5) selectable markers that can be used to select cells that have stably integrated the expression vector; and (6) plasmid backbone sequences to permit propagation in bacterial cells, etc. All eukaryotic expression systems known to date harbor several of the above-mentioned features (Kaufman, R. J., Methods in Enzymol. 185:487–511 (1990); Kriegler. M., Methods in Enzymol. 185:512–526 (1990)). Furthermore, all eukaryotes use similar mechanisms for the extracellular secretion of proteins (Barritt, G. J., ed. 1992 in "Communication within Animal Cells", pp. 42–48; Lewin, B. ed., 1994 in Genes V, pp. 289–293). Consequently, the rapid secretion potential conferred by Vtgss is not limited to a Drosophila expression system. Other expression systems based on eukaryotic host cells (e.g., other Drosophila host cells; baculovirus systems; other eukaryotic host cells, including mammalian, avian, reptilian, piscine, invertebrate (see Examples 2–4) and yeast (see Example 6)) can be used with the vectors of the invention.

EXAMPLE 2

Inducible Expression and Secretion of the Recombinant VtgssCAT and VtgssEGFP Reporters From Mammalian Cells We have thus constructed-a reporter CAT system (FIGS. 5A–5G) that uses the secretory signal of the O. aureus vitellogenin gene (Vtgss). The excellent secretory signal provides quantitative secretion of the CAT reporter protein into the culture medium, and thus it is not necessary to prepare a cell lysate to assay for the reporter protein. An investigator is thus provided with an easy assay for CAT activity and so can retain methodology that he/she has previously established in the laboratory. This permits easy comparison with data previously obtained using a CAT reporter protein.

The psp-VtgCAT (FIGS. 5D and 5E) and ERU-psp-VtgCAT (FIG. 5F) vectors were constructed by typical methods. The psp-VtgCAT has the pSEAP-Promoter vector backbone, but the SEAP gene is replaced by the recombinant VtgCAT gene. The ERU-psp-VtgCAT is psp-VtgCAT with the estrogen response unit from a Xenopus vitellogenin B1 gene (kindly provided by Professor W. Wahli, Switzerland) inserted upstream of the SV40 promoter. These constructs were co-transfected together with chicken estrogen receptor cDNA and pSEAP control DNA into various mammalian cell lines (e.g., CHO, NIH/3T3 & COS). This allows the testing of $E_2$-inducibility of the ERU-psp-VtgCAT. The secreted VtgCAT reporter protein was assayed by CAT ELISA (Boehringer Mannheim) (FIG. 6). To verify that the level of the secreted VtgCAT in the culture medium is directly proportional to changes in intracellular concentrations of VtgCAT mRNA, a Northern blot was performed under $E_2$-stimulation over a time course (FIG. 7). The results indicate that VtgCAT is efficiently secreted from the cells, and the levels of VtgCAT in the culture medium are directly proportional to changes in intracellular concentration of VtgCAT mRNA. Furthermore, the increase in VtgCAT can be detected as early as 2 h after $E_2$-stimulation. Importantly, the decrease in VtgCAT transcript after 24 h is also reflected by a lower amount of VtgCAT protein. This indicates that there is no delay in VtgCAT secretion. Thus, the Vtgss signal acts to immediately secrete the protein out of the mammalian cells.

pVtgEGFP, a green fluorescent protein reporter construct (FIGS. 8A–8C) was transiently expressed in COS cells. Vtgss also efficiently secreted the EGFP fluorescent protein into the culture medium (FIG. 8D).

EXAMPLE 3

Inducible Expression and Secretion of Recombinant CAT Reporter From Other Mammalian Cells (NIH/3T3 and CHO-B)

Estrogen-inducibility of ERU-psp-VtgssCAT was also demonstrated in other mammalian cell lines. NIH/3T3 (normal mouse fibroblast cells) and CHO-B (Chinese hamster ovary cells) were transfected as described in Example 3. Three time points were assayed for VtgssCAT secretion into the culture medium, 0, 6 and 24 h post estrogen induction. Peak expression of VtgssCAT was at 24 h. NIH/3T3 and CHO-B cells exhibited a 4-fold and 5.5-fold increase in VtgssCAT (FIG. 9). The results show that the estrogen-responsiveness, production and secretion of VtgssCAT is not limited to COS-1 cells.

EXAMPLE 4

Inducible Expression and Secretion of Recombinant CAT Reporter From Piscine Cells Co-transfection of the ERU-psp-VtgCAT construct with chicken estrogen receptor cDNA into a piscine cell line (e.g., Carp Epithelial cells, EPC) also resulted in estrogen-inducible expression and secretion of the CAT reporter protein into the culture medium (FIG. 10). EPC were cultured at a low temperature of 25° C. A 3-fold increase in VtgCAT can be detected by 24 h after estrogen-induction. The low metabolic rate of EPC likely explains the lower induction of VtgCAT compared to the levels observed in Example 3. Nonetheless, this experiment shows the efficiency of production and secretion of VtgCAT conferred by Vtgss. Furthermore, the Vtgss-directed secretion process is applicable to all eukaryotic cells; it is not limited to mammalian cells.

EXAMPLE 5

Expression of VtgCAT Reporter in S. cerevisiae (Strain DY150)

The VtgCAT reporter was inserted downstream of the strong phosphoglycerate kinase (PGK) promoter (FIG. 11).

The PGK promoter drives high constitutive expression of a heterologous protein. The plasmid provides for two selectable traits, URA3 and leu2-d. Expression of VtgCAT was monitored in yeast grown in a rich YEPD medium and synthetic minimal medium (MM). From FIG. 12, it is clear that production and secretion of VtgCAT occurred as early as 24 h. The amount of VtgCAT detected in the both kinds of culture medium is comparable. However, VtgCAT production and secretion appear to decrease by 48 h, particularly, for yeast grown in MM. By 48 h, the pH of the media has dropped to below the optimum of 5–6. This affects the growth of the transformants, and hence, production of VtgCAT. Adjusting the pH back to 5 resulted in a tremendous increase in VtgCAT in the culture media. Thus, the growth condition is important for efficient secretion of VtgCAT from yeast. We envisage that cultivation of recombinant yeast in a fermenter enables better control of growth conditions and consequently secretion of even higher amounts of VtgCAT into the culture medium. It is important to note that "secretion" in this application includes export of recombinant protein(s) into the periplasmic space, as well as through it into the culture medium, of a recombinant host cell that has a cell wall. In such instances, the "cell lysate" fraction will include proteins localized in the periplasmic compartment. In this particular example, a large proportion of the VtgCAT is found to accumulate in the periplasm. Use of wall-less mutants of yeast (or other fungi) host cells would prevent accumulation of the heterologous proteins in the periplasm. Such wall-less mutants are known in the art.

EXAMPLE 6

Inducible Expression and Secretion of Vtgss-p-lactamase From Bacteria

Ampicillin binds to and inhibits a number of enzymes in the bacterial membrane that are involved in the synthesis of cell wall. The ampicillin resistance gene carried on a plasmid codes for an enzyme (β-lactamase) that is secreted into the periplasmic space of the bacterium, where it catalyzes hydrolysis of the β-lactam ring with concomitant detoxification of ampicillin. To demonstrate the universality of Vtgss to direct secretion of recombinant proteins in bacteria, the native secretory signal of β-lactamase was replaced with Vtgss. The expression of this new fusion enzyme (Vtg-β-lactamase) is under the control of an arabinose-inducible promoter (e.g., araBAD promoter).

A β-lactamase gene was isolated by PCR using a blactfor forward primer which was designed to prime the start of the mature protein (i.e., to exclude the native secretory signal, see, FIGS. 13, 14A and 14B). Consequently, the only means of survival for pBADVtgblactKana transformants was when Vtgss correctly directs the secretion of the "truncated" β-lactamase into the periplasmic space for hydrolysis of ampicillin. Sufficient functional β-lactamase must be secreted into the periplasm to effectively hydrolyze ampicillin before the latter enters the cell or the host cells will die.

Expression of the β-lactamase in the periplasm was assayed by plating transformants on agar plates containing ampicillin and varying amount of arabinose. In the absence of arabinose (0.2% glucose) or in the presence of only 0.0002% arabinose, no colonies are seen. This is due to the insufficient expression and/or secretion of Vtg-β-lactamase under these conditions. When the amount of arabinose was increased (0.002 to 0.2% ,arabinose), a dose-dependent expression and secretion of Vtg-β-lactamase was observed which is reflected by the appearance of bacterial colonies on the agar plates (FIG. 15). It is envisaged that secretion of recombinant protein conferred by Vtgss will also apply for both Gram-positive and Gram-negative bacteria, since they share similarities in their secretory mechanisms (Lewin, B., ed., 1994 in "Genes V", pp. 298–299).

Figure 18:
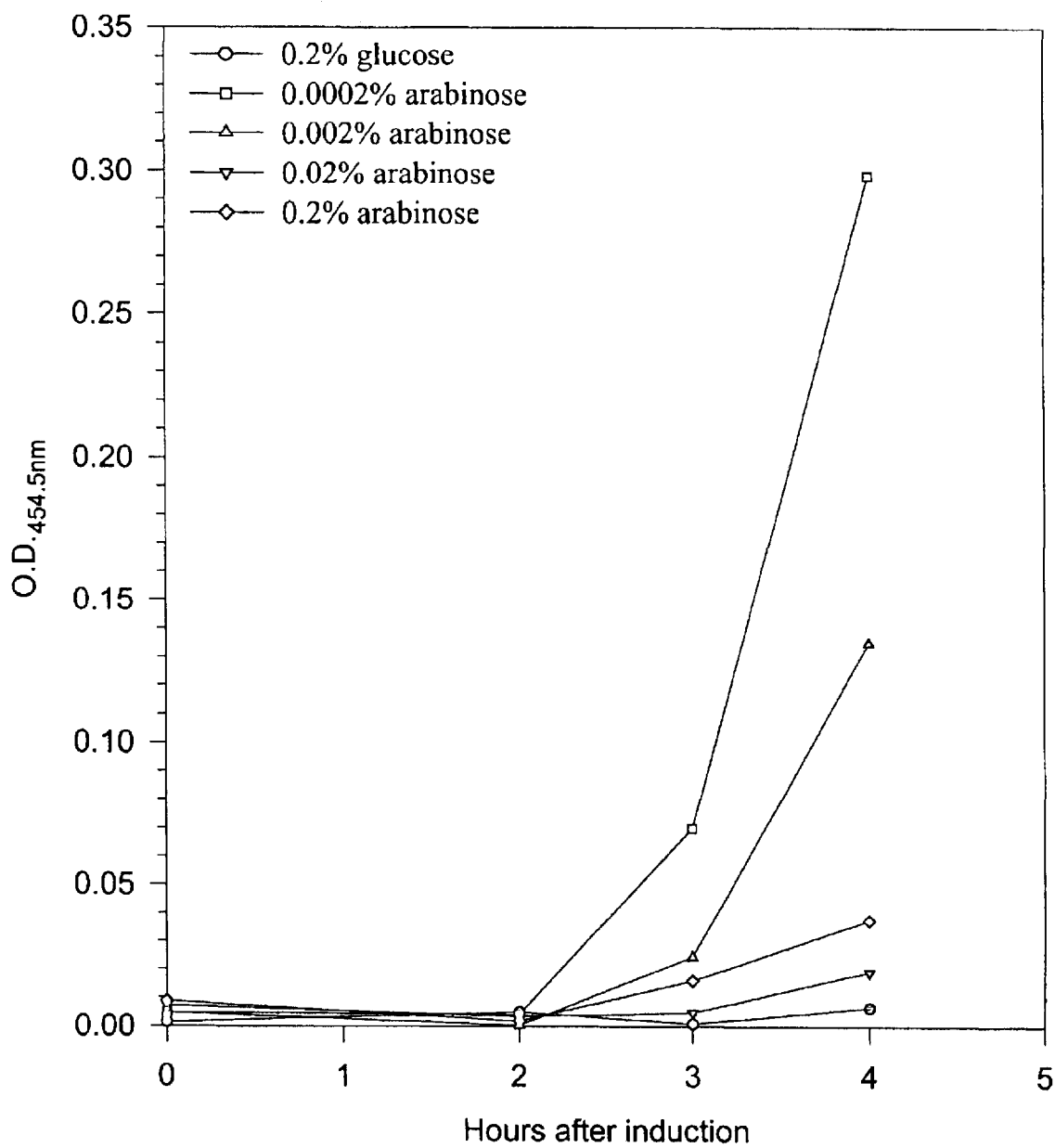

The arabinose-induced vector with Vtgss is capable of directing secretion of Vtg-β-lactamase into the periplasm as well as out of the bacteria into the culture medium (FIGS. 16–18), both of which caused the hydrolysis of ampicillin, hence the survival of positive clones carrying the Vtgss signal. The expression and secretion of Vtg-β-lactamase in this instance is strongly influenced by the bacterial growth rate and rate of transcription induction. Nonetheless, the Vtgss is a useful system for convenient screening/reporting of genetically-engineered clones harboring selectable marker(s)/enzymes (such as β-lactamase) to be expressed as an indicator. In the present example, the arabinose-induced growth of the positive clones in the presence of ampicillin selection is a convenient visual screen.

EXAMPLE 7

Rate of VtgCAT and Vtg-Gal Secretion in COS-1 Cells

Figure 19:
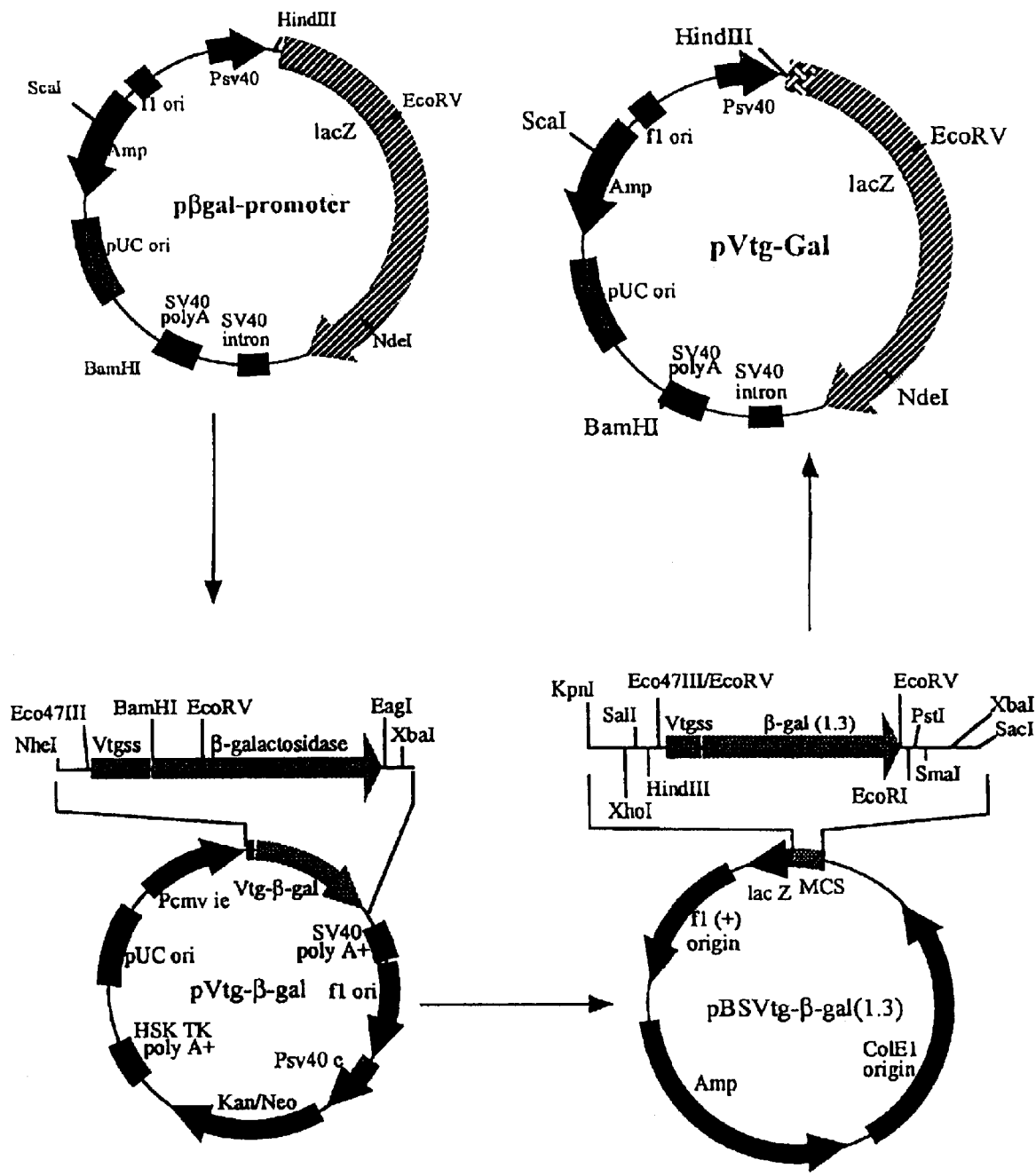
Figure 20:
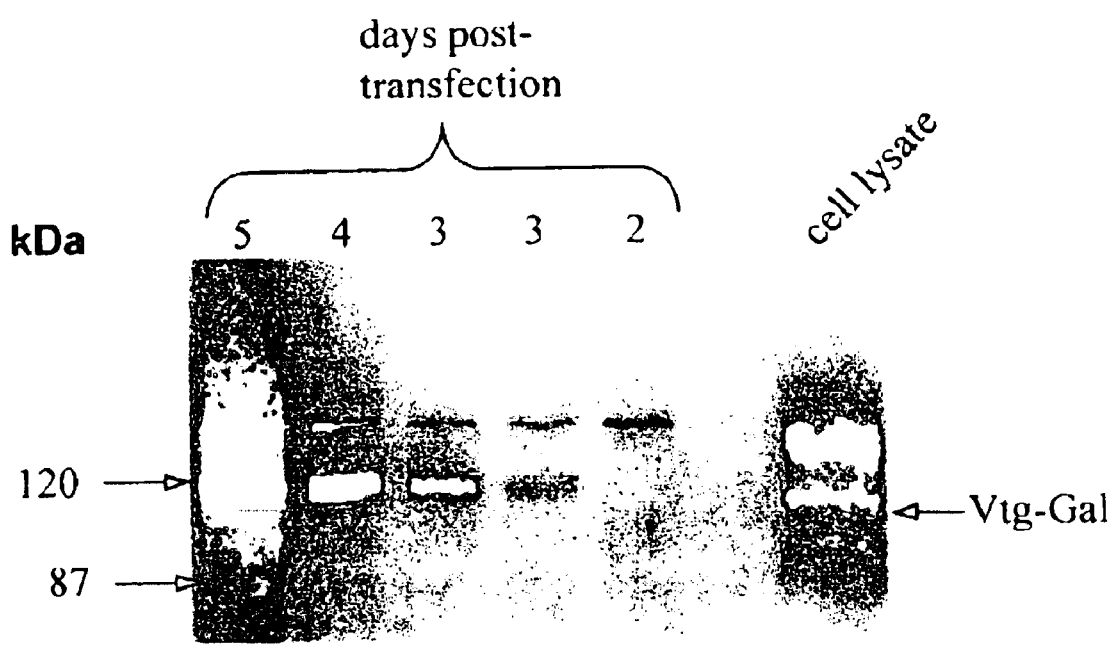

The construct, pVtg-Gal, which harbors a truncated β-galactosidase gene cloned downstream of Vtgss (FIG. 19) produced and secreted the recombinant Vtg-Gal into the medium when transfected into COS-1 cells. Western blot analysis using mouse anti-β-galactosidase identified a ~116 kDa recombinant Vtg-Gal in the culture medium of transfected COS-1 cells (see FIG. 20). Thus, Vtgss has the potential to direct secretion of a large heterologous protein.

Figure 21:
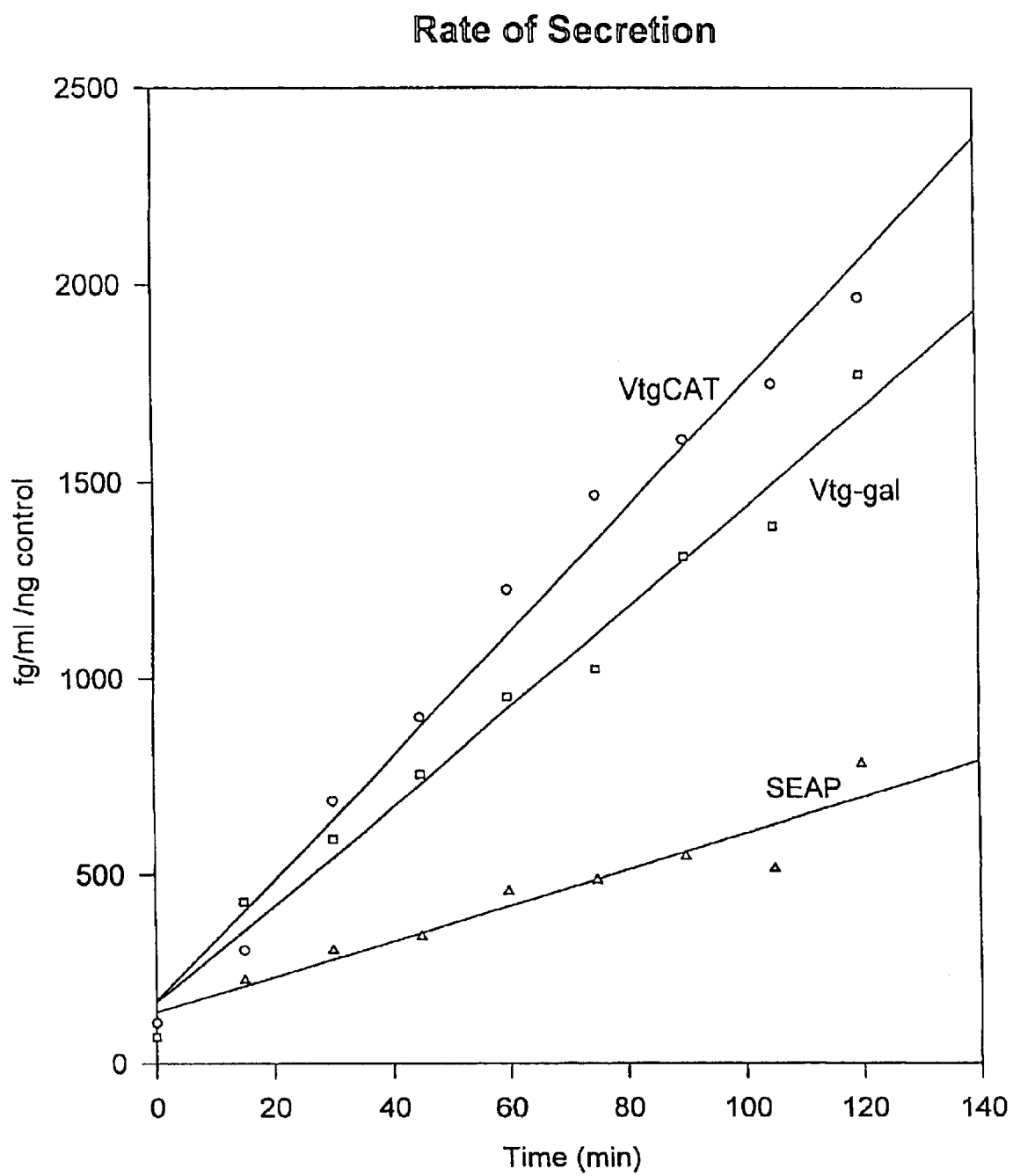

The amount of Vtgss-fusion protein secreted at various time intervals was determined using a standard curve created using the positive control provided by the kits. The rate f secretion was determined by the gradient of best-fit line when amount of secreted protein was plotted against time (FIG. 21). The mean rate of VtgCAT secretion was determined to be 165.778 fg/ml VtgCAT, β-galactosidase/min±0.118 fg/ml/min. The mean rate of Vtg-Gal secretion was determined to be 12.14 fg/ml Vtg-Gal/ng SEAP/min±0.091 fg/ml/min. In comparison SEAP was secreted at a rate of 4.763 fg/ml SEAP/ng β-galactosidase/min±0.061 fg/ml/min. The rate of VtgCAT and Vtg-Gal secretion were almost 3-fold higher than SEAP. This would prove very critical for experiments investigating short term or rapid transcriptions. Once again, this shows that Vtgss is capable of directing rapid secretion of recombinant proteins regardless of their size. The values for VtgCAT and SEAP secreted were normalized by, β-galactosidase production. Similarly, the values for secreted Vtg-Gal were normalized with SEAP.

The above examples are merely illustrative of the invention and are not to be understood as limiting it. Rather, the scope of the present invention is defined by the claims following. All references of the patent and scientific periodical literature cited above are hereby incorporated in their entirety by reference by such citation.

What is claimed is:

1. An isolated nucleic acid comprising a nucleotide sequence encoding a secretory signal sequence comprising the amino acid sequence SEQ ID NO:10, or variants of said amino acid sequence that comprise conservative replacements thereof that retain the biological activities of directing secretion of a fusion protein from a cell and cleavage of the secretory signal sequence from the fusion protein, wherein the variations in said variants (a) relate to the glycine and aspartic acid residues constituting the cleavage site, and in said variations aspartic acid is replaced by glutamic acid and/or glycine is replaced by alanine or valine, (b) constitute at most 4 additions, or deletions of amino acids in the secretory sequence, (c) result in the stretch of hydrophobic amino acids in the interior of the secretory sequence being 10–15 amino acids long, and/or (d) constitute the overall substitution of fewer than 7 amino acids in the secretory sequence.

2. The isolated nucleic acid of claim 1, wherein said secretory signal sequence comprises the amino acid sequence SEQ ID NO:10, or variants of said amino acid sequence wherein the arginine at the second position is replaced by lysine and/or the glycine at the fifteenth position is replaced by alanine or valine and/or the aspartic acid at the sixteenth position is replaced by glutamic acid.

3. The isolated nucleic acid of claim 2, wherein the amino acid sequence is the amino acid sequence of SEQ ID NO:10.

4. The isolated nucleic acid of claim 1, wherein the nucleotide sequence encoding the secretory signal sequence is SEQ ID NO:11.

5. The isolated nucleic acid of claim 1, wherein the cell from which secretion is directed is a eukaryotic cell.

6. The isolated nucleic acid of claim 1, wherein the cell from which secretion is directed is a prokaryotic cell.

7. The isolated nucleic acid of claim 3, wherein the secretory signal sequence is cleaved between the glycine and aspartic acid residues in the valine-glycine-aspartic acid-glutamine portion thereof.

8. An isolated nucleic acid comprising a nucleotide sequence encoding a fusion protein comprising a secretory signal sequence and a desired heterologous protein, wherein said secretory signal sequence, comprises the amino acid sequence SEQ ID NO:10, or variants of said amino acid sequence that comprise conservative replacements thereof that retain the biological activities of directing secretion of a fusion protein from a cell and cleavage of the secretory signal sequence from the fusion protein, wherein the variations in said variants (a) relate to the glycine and aspartic acid residues constituting the cleavage site, and in said variations aspartic acid is replaced by glutamic acid and/or glycine is replaced by alanine or valine, (b) constitute at most 4 additions or deletions of amino acids in the secretory sequence, (c) result in the stretch of hydrophobic amino acids in the interior of the secretory sequence being 10–15 amino acids long, and/or (d) constitute the overall substitution of fewer than 7 amino acids in the secretory sequence, and
wherein the desired heterologous protein is joined to the carboxy-terminus of the secretory signal sequence, either directly or by a linking amino acid sequence.

9. The isolated nucleic acid of claim 8, wherein said secretory signal sequence comprises the amino acid sequence SEQ ID NO:10, or variants of said amino acid sequence wherein the arginine at the second position is replaced by lysine and/or the glycine at the fifteenth position is replaced by alanine or valine and/or the aspartic acid at the sixteenth position is replaced by glutamic acid.

10. The isolated nucleic acid of claim 9, wherein said secretory signal sequence comprises the amino acid sequence of SEQ ID NO:10.

11. The isolated nucleic acid of claim 10, wherein the nucleotide sequence encoding the secretory signal sequence is SEQ ID NO:11.

12. The isolated nucleic acid of claim 8 wherein said desired heterologous protein is a reporter protein.

13. The isolated nucleic acid of claim 12, wherein the reporter protein is selected from the group consisting of chloramphenicol aminotransferase, green fluorescent protein or another aequorin, β-amylase, β-lactamase, luciferase, glucuronidase, alkaline phosphatase, and β-galactosidase.

14. The isolated nucleic acid of claim 8 wherein said desired protein is a lipopolysaccharide-binding protein.

15. The isolated nucleic acid of claim 14, wherein the lipopolysaccharide-binding protein is Factor C.

16. A recombinant vector comprising the isolated nucleic acid of any one of claims 8–11.

17. A host cell transformed with the recombinant vector of claim 16.

18. The recombinant host cell of claim 17, wherein said cell is selected from the group consisting of a bacterial cell, a COS cell, a Chinese hamster ovary (CHO) cell, a NIH/3T3 cell, a Schneider 2 cell, a *S. cerevisiae* cell, and an endothelial progenitor cell (EPC).

19. A method for producing a desired protein comprising culturing a host cell of claim 17 under conditions wherein the desired protein is secreted from the host cell, and recovering the desired protein from the culture medium.

20. A fusion protein comprising
(i) a secretory signal sequence polypeptide comprising the amino acid sequence SEQ ID NO:10, or variants of said amino acid sequence that comprise conservative replacements thereof that retain the biological activities of directing secretion of a fusion protein from a cell and cleavage of the secretory signal sequence from the fusion protein, wherein the variations in said variants (a) relate to the glycine and aspartic acid residues constituting the cleavage site, and in said variations aspartic acid is replaced by glutamic acid and/or glycine is replaced by alanine or valine, (b) constitute at most 4 additions or deletions of amino acids in the secretory sequence, (c) result in the stretch of hydrophobic amino acids in the interior of the secretory sequence being 10–15 amino acids long, and/or (d) constitute the overall substitution of fewer than 7 amino acids in the secretory sequence, and (ii) a heterologous polypeptide.

21. The fusion protein of claim 20, wherein said secretory signal sequence polypeptide comprises the amino acid sequence SEQ ID NO:10, or variants of said amino acid sequence wherein the arginine at the second position is replaced by lysine and/or the glycine at the fifteenth position is replaced by alanine or valine and/or the aspartic acid at the sixteenth position is replaced by glutamic acid.

22. The fusion protein of claim 21, wherein said secretory signal sequence comprises the amino acid sequence of SEQ ID NO:10.

23. The fusion protein of claim 22, wherein the nucleotide sequence encoding the secretory signal sequence is SEQ ID NO:11.

24. The fusion protein of claim 20, wherein the heterologous polypeptide is a lipopolysaccharide binding protein.

25. The fusion protein of claim 20, wherein the heterologous polypeptide is a protein selected from the group consisting of chloramphenicol aminotransferase, green fluorescent protein or another aequorin, β-amylase, β-lactamase, luciferase, glucuronidase, alkaline phosphatase, and β-galactosidase.

* * * * *